US012784087B1

(12) United States Patent
Tuan et al.

(10) Patent No.: US 12,784,087 B1
(45) Date of Patent: *Nov. 3, 2026

(54) FACIAL SCANNING TOOL FOR SKINCARE AND COSMETIC PRODUCTS

(71) Applicant: Sephora USA, Inc., San Francisco, CA (US)

(72) Inventors: Lucie Tuan, Oakland, CA (US); Savio Thattil, Pleasanton, CA (US); Julie Borstein, Burlingame, CA (US); Margarita Arriagada, Studio City, CA (US)

(73) Assignee: Sephora USA, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/923,362

(22) Filed: Oct. 22, 2024

Related U.S. Application Data

(63) Continuation of application No. 17/809,511, filed on Jun. 28, 2022, now Pat. No. 12,125,245, which is a continuation of application No. 13/924,551, filed on Jun. 22, 2013, now Pat. No. 11,373,336.

(60) Provisional application No. 61/826,488, filed on May 22, 2013.

(51) Int. Cl.

| | |
|---|---|
| ***G06Q 30/0601*** | (2023.01) |
| ***A61B 5/00*** | (2006.01) |
| ***G01J 3/50*** | (2006.01) |
| ***G06F 16/23*** | (2019.01) |
| ***G06F 16/24*** | (2019.01) |
| ***G06F 16/951*** | (2019.01) |
| ***G06F 16/9535*** | (2019.01) |
| ***G06T 7/90*** | (2017.01) |
| ***G06V 10/22*** | (2022.01) |
| ***G06V 40/16*** | (2022.01) |
| ***H04L 51/046*** | (2022.01) |

(52) U.S. Cl.

CPC ........... *G06Q 30/0627* (2013.01); *A61B 5/44* (2013.01); *G01J 3/50* (2013.01); *G06F 16/23* (2019.01); *G06F 16/24* (2019.01); *G06F 16/951* (2019.01); *G06F 16/9535* (2019.01); *G06Q 30/0625* (2013.01); *G06Q 30/0631* (2013.01); *G06Q 30/0641* (2013.01); *G06T 7/90* (2017.01); *G06V 10/22* (2022.01); *G06V 40/16* (2022.01); *H04L 51/046* (2013.01)

(58) Field of Classification Search

CPC ........................................................ G06T 7/90

USPC ........................................................... 348/77

See application file for complete search history.

(56) References Cited

U.S. PATENT DOCUMENTS

| | | | | |
|---|---|---|---|---|
| 7,738,032 | B2 | 6/2010 | Kollias et al. | |
| 2002/0065452 | A1 | 5/2002 | Bazin et al. | |
| 2007/0058860 | A1 | 3/2007 | Harville et al. | |
| 2007/0071314 | A1 | 3/2007 | Bhatti et al. | |
| 2008/0079843 | A1 | 4/2008 | Pote et al. | |
| 2010/0185064 | A1 * | 7/2010 | Bandic .................. | A61B 5/444 600/306 |

(Continued)

*Primary Examiner* — Amir Shahnami

(74) *Attorney, Agent, or Firm* — Aka Chan LLP

(57) ABSTRACT

A system allows people to more easily find products matching their skin tone. The system includes a scanning device to scan one or more spots of a person's skin. For example, three different spots can be scanned. The scan determines a skin-tone identifier for the person's skin. With this skin-tone identifier, the customer can view products that match their skin tone.

20 Claims, 29 Drawing Sheets

(56) References Cited

U.S. PATENT DOCUMENTS

| | | | |
|---|---|---|---|
| 2010/0322878 | A1 | 12/2010 | Stella et al. |
| 2012/0253224 | A1 | 10/2012 | Mir et al. |
| 2013/0250322 | A1 | 9/2013 | Kawabata et al. |
| 2013/0256505 | A1 | 10/2013 | Gomi et al. |

* cited by examiner 901 903

| | | RED SIDE | | | | | YELLOW SIDE | | | | |
|---|---|---|---|---|---|---|---|---|---|---|---|
| | | 5R | 4R | 3R | 2R | 1R | 1Y | 2Y | 3Y | 4Y | 5Y |
| FAIR | 01 | | | | | | 1Y01 | 2Y01 | 3Y01 | 4Y01 | 5Y01 |
| | 02 | | | | | 1R02 | 1Y02 | 2Y02 | 3Y02 | 4Y02 | 5Y02 |
| LIGHT | 03 | | | | 2R03 | 1R03 | 1Y03 | 2Y03 | 3Y03 | 4Y03 | 5Y03 |
| | 04 | 5R04 | 4R04 | 3R04 | 2R04 | 1R04 | 1Y04 | 2Y04 | 3Y04 | 4Y04 | 5Y04 |
| | 05 | 5R05 | 4R05 | 3R05 | 2R05 | 1R05 | 1Y05 | 2Y05 | 3Y05 | 4Y05 | 5Y05 |
| | 06 | 5R06 | 4R06 | 3R06 | 2R06 | 1R06 | 1Y06 | 2Y06 | 3Y06 | 4Y06 | 5Y06 |
| MEDIUM | 07 | 5R07 | 4R07 | 3R07 | 2R07 | 1R07 | 1Y07 | 2Y07 | 3Y07 | 4Y07 | 5Y07 |
| | 08 | | 4R08 | 3R08 | 2R08 | 1R08 | 1Y08 | 2Y08 | 3Y08 | 4Y08 | 5Y08 |
| | 09 | | 4R09 | 3R09 | 2R09 | 1R09 | 1Y09 | 2Y09 | 3Y09 | 4Y09 | 5Y09 |
| TAN | 10 | | | 3R10 | 2R10 | 1R10 | 1Y10 | 2Y10 | 3Y10 | 4Y10 | |
| | 11 | | | 3R11 | 2R11 | 1R11 | 1Y11 | 2Y11 | 3Y11 | 4Y11 | |
| DEEP | 12 | | | 3R12 | 2R12 | 1R12 | 1Y12 | 2Y12 | 3Y12 | | |
| | 13 | | | 3R13 | 2R13 | 1R13 | 1Y13 | 2Y13 | | | |
| DARK | 14 | | 4R14 | 3R14 | 2R14 | 1R14 | 1Y14 | | | | |
| | 15 | | 4R15 | 3R15 | 2R15 | 1R15 | | | | | |

FIGURE 9

FACIAL SCANNING TOOL FOR SKINCARE AND COSMETIC PRODUCTS

CROSS-REFERENCE TO RELATED APPLICATIONS

This patent application is a continuation of U.S. patent application Ser. No. 17/809,511, filed Jun. 28, 2022, issued as U.S. Pat. No. 12,125,245 on Oct. 22, 2024, which is a continuation of U.S. patent application Ser. No. 13/924,551 filed Jun. 22, 2013, issued as U.S. Pat. No. 11,373,336 on Jun. 28, 2022, which claims the benefit of U.S. patent application 61/826,488, filed May 22, 2013. These applications are incorporated by reference along with all other references cited in this application.

BACKGROUND OF THE INVENTION

This invention relates to cosmetics and more specifically, to techniques for selecting one or more cosmetic products based on the individual requirements of a specific user.

For people in the market for cosmetic products, the process can be daunting. Cosmetic products are applied on different areas of the human body, oftentimes used to improve the attractiveness of its user. But there are a myriad of different types of products out on the market, with products spanning across a wide spectrum of uses. From skin-care creams, foundations (e.g., moisturizer, mousse, liquid, cream-to-powder, concealer, minerals, or other types) lotions, hair sprays and gels, powders, perfumes, lipsticks, cuticle (or fingernail) and nail polish, eye and facial makeup, hair colors, bath oils, bubble baths, and other products, the choices of which to use can be overwhelming.

Even among each type of cosmetic product, making a right decision can still be elusive. For example, an intensive moisturizer may be suitable for someone with drier skin, but inappropriate for someone with oilier skin since it can cause an unattractive sheen. In another example, foundations come in many different shades of colors for different skin tones. Selecting the wrong foundation for a given skin tone can result in an unattractive appearance, such as colors improperly cast on a user's face or a splotchy appearance.

Oftentimes, people rely on word-of-mouth from trusted persons such as close friends, coworkers or family members to select which products to purchase. This advice can be helpful, but these trusted persons may only be knowledgeable with their own cosmetic decisions that may not apply to another.

However, finding knowledgeable help for all a person's cosmetic questions on a variety of products can be difficult. Many department stores and stand-alone cosmetic sales locations include sales associates that assist customers. Yet this assistance may come with sales pitches and other pressure sales tactics that customers do not feel comfortable with. Also, similar to trusted persons, these sales associates can be most familiar with products they are most exposed to and not what an actual customer may need.

Therefore, there is a need for a better method to determine what cosmetics are best suited for a person. This way, the person can feel confident in their cosmetic decisions and more willing to repurchase their selected cosmetic products.

BRIEF SUMMARY OF THE INVENTION

A system allows people to more easily find products matching their skin tone, including a scanning device to scan one or more spots of a person's skin. For example, three different spots can be scanned. The scan determines a skin-tone identifier for the person's skin. This skin-tone identifier is used by a software program (e.g., executing on a tablet computer) to determine and output a listing of products that are appropriate for the person's skin tone.

A method to select cosmetic products with great accuracy, based on a customer's skin tone. For example, some systems use the ethnicity and subjective determinations to determine broad characteristics of a customer to identify a set of basic tones and products the customer may be suited for. However, the system receives the actual skin tone of the customer based on a skin tone color set to determine a skin tone identifier for the customer. The skin tone color set is indexed with one or more cosmetic products to provide suggestions matching the customer's skin tone.

In an implementation, the system can assist customers in determining a right shade of foundation for their skin. Foundations are used to hide imperfections, absorb oil, help with dry spots, even out skin tone, and help make fine lines and wrinkles less noticeable. The system helps the customer choose the right shade of foundation by matching the customer's skin tone to foundations in the system. For example, the system is adapted to receive the customer's skin tone information in more than one way. The skin tone information can be indexed according to a skin tone color standard, and the skin tone color standard indexed to products.

In an implementation, the system includes: providing a skin tone color space, where the skin tone color space includes skin tone identifiers and each skin tone identifier corresponds to a skin tone found in a population sample; initializing a scanning device; positioning the scanning device to take a first measurement at a first location of a customer; positioning the scanning device to take a second measurement at a second location of the customer, where the first and second locations are different locations of the customer; and blending to determine a skin tone identifier in the skin tone color space for the customer based on the first and second measurements.

In various implementations, the system includes positioning the scanning device to take a third measurement at a third location of the customer, where the third location is different than the first and second locations. The blending to determine a skin tone identifier is based on the third measurement. The system includes where the first location includes a forehead of the customer. The second location includes a cheekbone of the customer. The third location includes an area below a lip of the customer.

The skin tone color space is stored on nonvolatile memory at the scanning device. The system includes where the initializing the scanning device includes calibrating the device to a reference point. The system includes where before the reference point is a predefined reference point before the calibrating. The system where the calibrating the device to a reference point includes taking a scan of a color swatch of the predefined reference point. Initializing the scanning device includes cleaning a scanning portion of the scanning device. The first and second locations are free of facial blemishes. The system can include where the first and second locations are free of irregular pigmentation.

In an implementation, the system includes: providing a skin tone color space, where the skin tone color space includes skin tone identifiers; initializing a scanning device; positioning the scanning device to take a first measurement of a customer; positioning the scanning device to take a second measurement of the customer; mixing to determine a skin tone identifier in the skin tone color space for the customer based on the first and second measurements; and displaying on a screen the skin tone identifier.

The system can include where the screen is a screen of the scanning device. The system can include positioning the scanning device to take a third measurement of the customer.

In an implementation, the system includes: a memory portion, storing a skin tone color space, where the skin tone color space includes skin tone identifiers and each skin tone identifier corresponds to a skin tone found in a population sample; a scanning portion with light emitting elements and a photosensitive sensor; and a processing portion to determine skin tone identifiers, including: receiving at least two skin tone measurements; and averaging the at least two skin tone measurements to determine a skin tone identifier based on the skin tone color space.

The system can include a display portion displaying determined skin tone identifiers. The system can include where the memory portion includes storing skin tone identifiers for a first and second customers. The system can include where the at least two skin tone measurements are received from the scanning portion.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 9 shows a skin tone color set in an implementation of the system.

DETAILED DESCRIPTION OF THE INVENTION

The system includes a cosmetic product selection tool, which uses skin tone to determine suitable products for customers. Ethnicity is not determinative when selecting suitable cosmetic products; there are more factors in the physiology of the skin that determine color (e.g., hemoglobin, sun exposure, freckles, skin conditions, sun burn, or excess or absence of melanin). The system can be based off a skin tone color set that indexes skin tone colors such as Pantone's Skintone Library, although other skin tone color sets can be used by the system. A specific implementation is a foundation matching system that is used to determine an appropriate color of a foundation (e.g., a cosmetic foundation) to match a person's skin tone.

Figure 1:
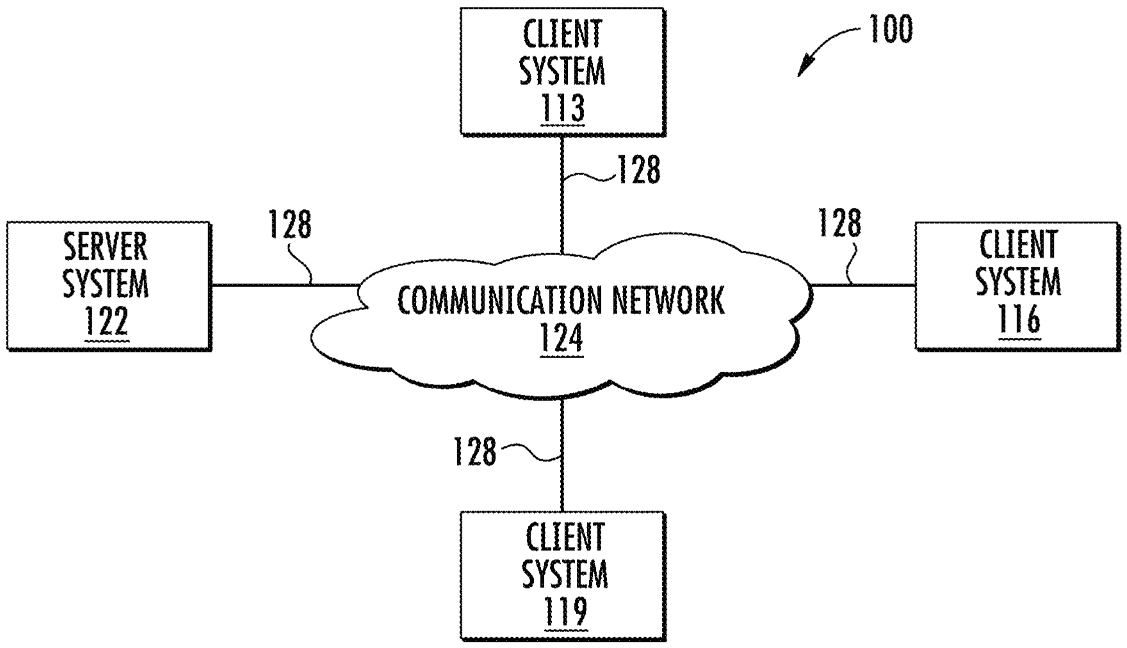
FIG. 1 shows a simplified block diagram of a distributed computing network connecting a server and clients.

FIG. 1 is a simplified block diagram of a distributed computer network 100 incorporating an embodiment of the present invention. Computer network 100 includes a number of client systems 113, 116, and 119, and a server system 122 coupled to a communication network 124 via a plurality of communication links 128. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information. Communication links 128 may be DSL, Cable, Ethernet or other hardwire links, passive or active optical links, 3G, 3.5G, 4G and other mobility, satellite or other wireless communications links, wave propagation links, or any other mechanisms for communication of information.

Various communication protocols may be used to facilitate communication between the various systems shown in FIG. 1. These communication protocols may include VLAN, MPLS, TCP/IP, Tunneling, HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, a intranet, a private network, a public network, a switched network, and combinations of these, and the like.

Distributed computer network 100 in FIG. 1 is merely illustrative of an embodiment incorporating the present invention and does not limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server system which provides the information. For this reason, server systems typically have more computing and storage capacity than client systems. However, a particular computer system may act as both as a client or a server depending on whether the computer system is requesting or providing information. Additionally, although aspects of the invention has been described using a client-server environment, it should be apparent that the invention may also be embodied in a stand-alone computer system.

Server 122 is responsible for receiving information requests from client systems 113, 116, and 119, performing processing required to satisfy the requests, and for forwarding the results corresponding to the requests back to the requesting client system. The processing required to satisfy the request may be performed by server system 122 or may alternatively be delegated to other servers connected to communication network 124.

Client systems 113, 116, and 119 enable users to access and query information stored by server system 122. In a specific embodiment, the client systems can run as a stand-alone application such as a desktop application or mobile smartphone or tablet application. In another embodiment, a "web browser" application executing on a client system enables users to select, access, retrieve, or query information stored by server system 122. Examples of web browsers include the Internet Explorer browser program provided by Microsoft Corporation, Firefox browser provided by Mozilla, Chrome browser provided by Google, Safari browser provided by Apple, and others.

In a client-server environment, some resources (e.g., files, music, video, or data) are stored at the client while others are stored or delivered from elsewhere in the network, such as a server, and accessible via the network (e.g., the Internet). Therefore, the user's data can be stored in the network or "cloud." For example, the user can work on documents on a client device that are stored remotely on the cloud (e.g., server). Data on the client device can be synchronized with the cloud.

Figure 2:
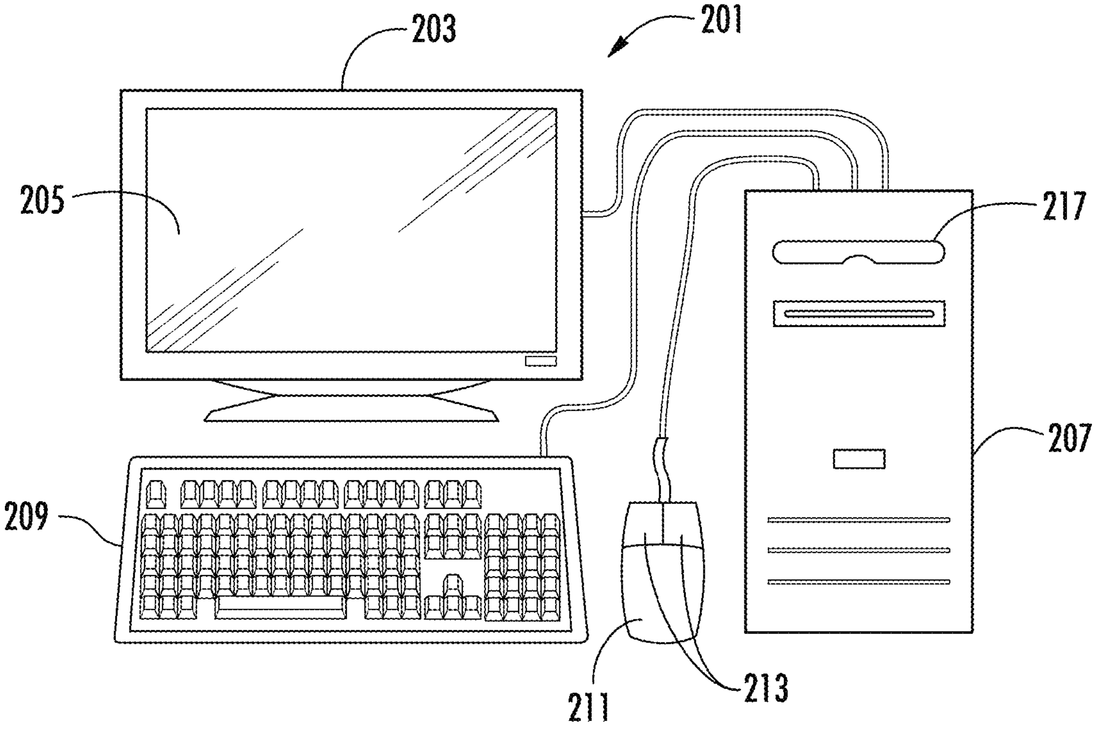
FIG. 2 shows a more detailed diagram of a client or server of the system.

FIG. 2 shows an exemplary client or server system of the present invention. In an embodiment, a user interfaces with the system through a computer workstation system, such as shown in FIG. 2. FIG. 2 shows a computer system 201 that includes a monitor 203, screen 205, enclosure 207 (may also be referred to as a system unit, cabinet, or case), keyboard or other human input device 209, and mouse or other pointing device 211. Mouse 211 may have one or more buttons such as mouse buttons 213.

It should be understood that the present invention is not limited any computing device in a specific form factor (e.g., desktop computer form factor), but can include all types of computing devices in various form factors. A user can interface with any computing device, including smartphones, personal computers, laptops, electronic tablet devices, global positioning system (GPS) receivers, portable media players, personal digital assistants (PDAs), other network access devices, and other processing devices capable of receiving or transmitting data.

For example, in a specific implementation, the client device can be a smartphone or tablet device, such as the Apple iPhone (e.g., Apple iphone 5), Apple iPad (e.g., Apple iPad or Apple iPad mini), Apple iPod (e.g., Apple ipod Touch), Samsung Galaxy product (e.g., Galaxy S series product or Galaxy Note series product), Google Nexus devices (e.g., Google Nexus 4, Google Nexus 7, or Google Nexus 10), and Microsoft devices (e.g., Microsoft Surface tablet).

Typically, a smartphone includes a telephony portion (and associated radios) and a computer portion, which are accessible via a touch screen display. There is nonvolatile memory to store data of the telephone portion (e.g., contacts and phone numbers) and the computer portion (e.g., application programs including a browser, pictures, games, videos, and music). The smartphone typically includes a camera (e.g., front facing camera or rear camera, or both) for taking pictures and video. For example, a smartphone or tablet can be used to take live video that can be streamed to one or more other devices.

Enclosure 207 houses familiar computer components, some of which are not shown, such as a processor, memory, mass storage devices 217, and the like. Mass storage devices 217 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive or solid state drive (SSD)), battery-backed-up volatile memory, tape storage, reader, and other similar media, and combinations of these.

A computer-implemented or computer-executable version or computer program product of the invention may be embodied using, stored on, or associated with computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software of the present invention may also be stored or reside on mass storage device 217 (e.g., hard disk, magnetic disk, tape, or CD-ROM). As a further example, code of the invention may be transmitted via wires, radio waves, or through a network such as the Internet.

Figure 3:
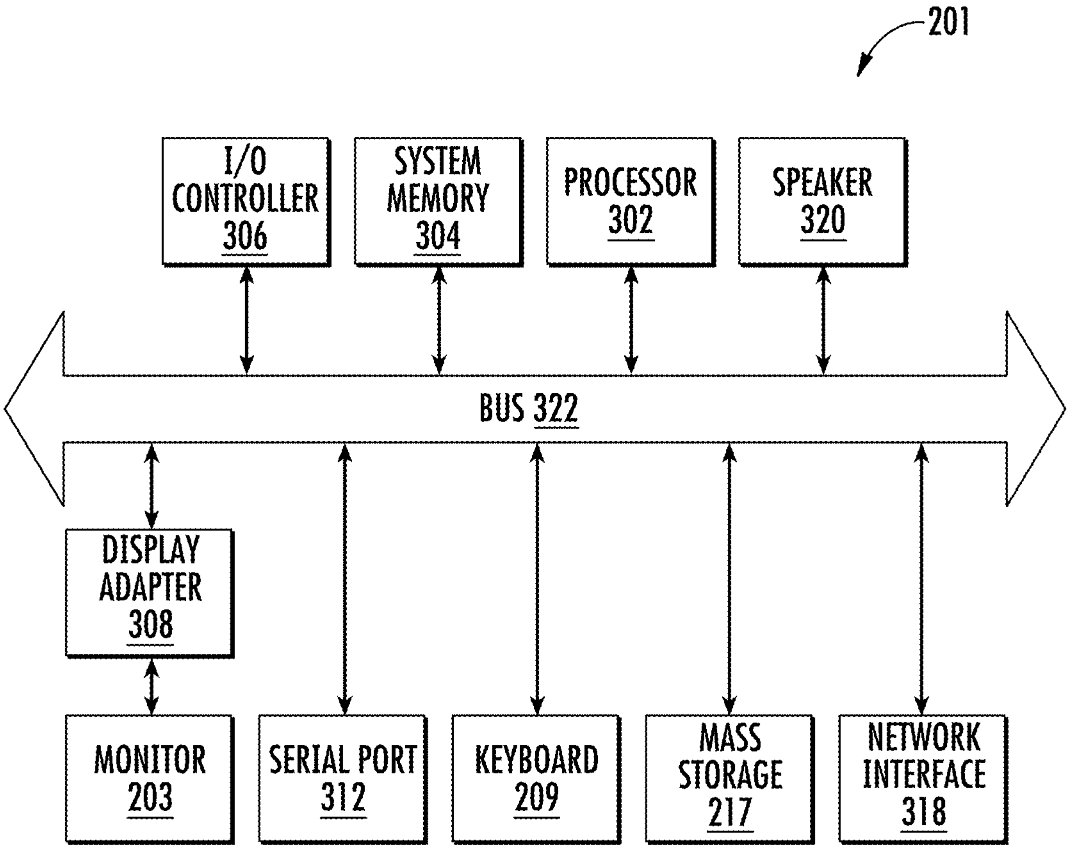
FIG. 3 shows a system block diagram of a client or server used to execute application programs.

FIG. 3 shows a system block diagram of computer system 201 used to execute the software of the present invention. As in FIG. 2, computer system 201 includes monitor 203, keyboard 209, and mass storage devices 217. Computer system 501 further includes subsystems such as central processor 302, system memory 304, input/output (I/O) controller 306, display adapter 308, serial or universal serial bus (USB) port 312, network interface 318, and speaker 320. The invention may also be used with computer systems with additional or fewer subsystems. For example, a computer system could include more than one processor 302 (i.e., a multiprocessor system) or a system may include a cache memory.

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. The processor may include multiple processors or a multicore processor, which may permit parallel processing of information. Computer system 201 shown in FIG. 2 is but an example of a computer system suitable for use with the present invention. Other configurations of subsystems suitable for use with the present invention will be readily apparent to one of ordinary skill in the art.

Computer software products may be written in any of various suitable programming languages, such as C, C++, C#, Pascal, Fortran, Perl, Matlab (from Math Works, www.mathworks.com), SAS, SPSS, JavaScript, AJAX, Java, Erlang, and Ruby on Rails. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of systems (e.g., Windows 95, 98, Me, Windows NT, Windows 2000, Windows XP, Windows XP x64 Edition, Windows Vista, Windows 7, Windows 8, Windows CE, Windows Mobile, Windows RT), Symbian OS, Tizen, Linux, HP-UX, UNIX, Sun OS, Solaris, Mac OS X, Apple IOS, Android, Alpha OS, AIX, IRIX32, or IRIX64. Other operating systems may be used. Microsoft Windows is a trademark of Microsoft Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11 g, 802.11i, 802.11n, 802.11ac, and 802.11ad, just to name a few examples), near field communication (NFC), radio-frequency identification (RFID), mobile or cellular wireless (e.g., 2G, 3G, 4G, 3GPP LTE, WiMAX, LTE, LTE Advanced, Flash-OFDM, HIPERMAN, iBurst, EDGE Evolution, UMTS, UMTS-TDD, 1xRDD, and EV-DO). For example, signals from a computer may be transferred, at least in part, wirelessly to components or other computers.

In an embodiment, with a web browser executing on a computer workstation system, a user accesses a system on the World Wide Web (WWW) through a network such as the Internet. The web browser is used to download web pages or other content in various formats including HTML, XML, text, PDF, and postscript, and may be used to upload information to other parts of the system. The web browser may use uniform resource identifiers (URLs) to identify resources on the web and hypertext transfer protocol (HTTP) in transferring files on the web.

In other implementations, the user accesses the system through either or both of native and nonnative applications. Native applications are locally installed on the particular computing system and are specific to the operating system or one or more hardware devices of that computing system, or a combination of these. These applications (which are sometimes also referred to as "apps") can be updated (e.g., periodically) via a direct internet upgrade patching mechanism or through an applications store (e.g., Apple iTunes and App store, Google Play store, and Windows Phone App store).

The system can run in platform-independent, nonnative applications. For example, client can access the system through a web application from one or more servers using a network connection with the server or servers and load the web application in a web browser. For example, a web application can be downloaded from an application server over the Internet by a web browser. Nonnative applications can also be obtained from other sources, such as a disk.

This application describes some specific flows, but it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data.

Figure 4:
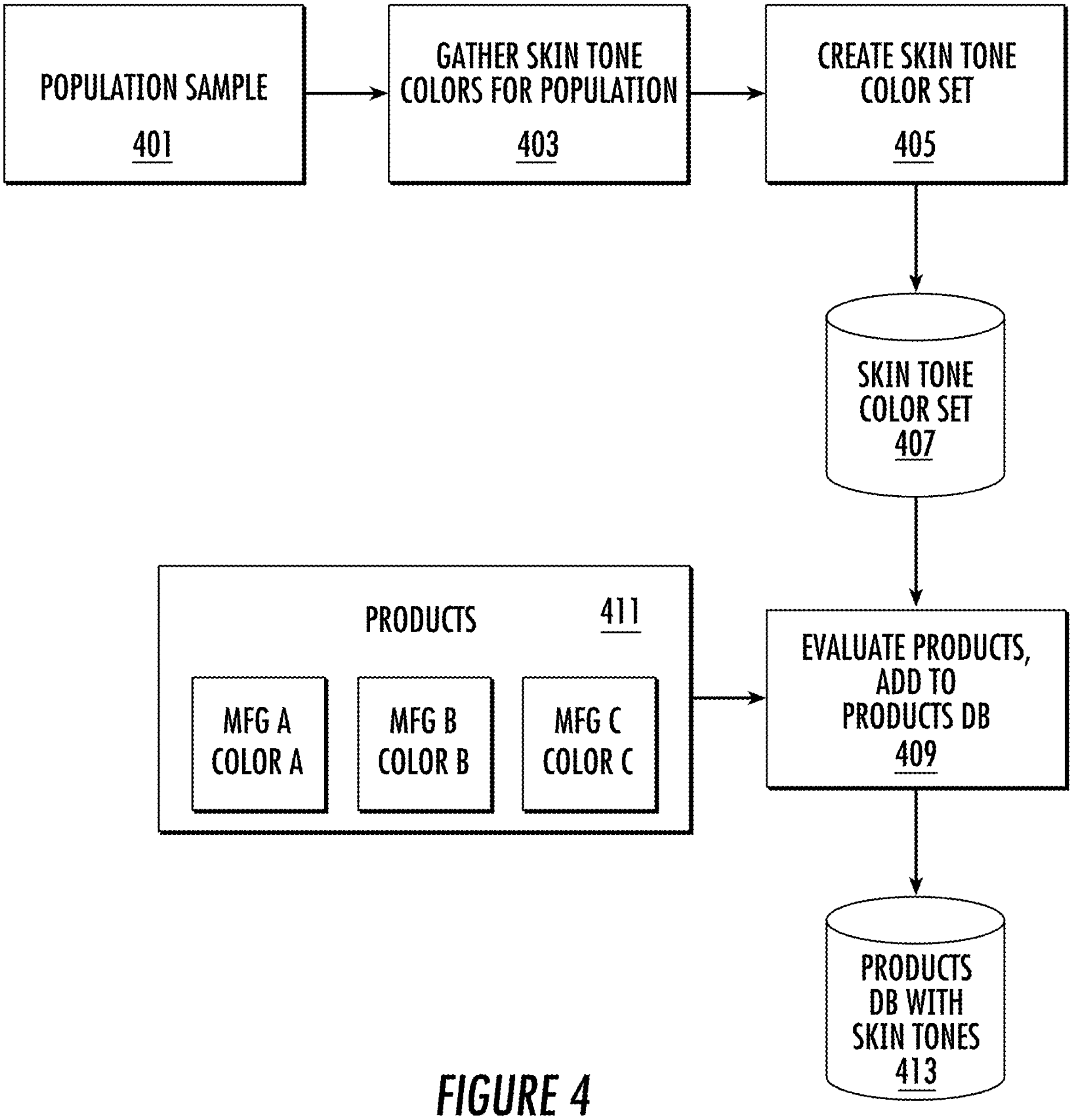
FIG. 4 shows a back end of a system for product matching based on skin tone.
Figure 5:
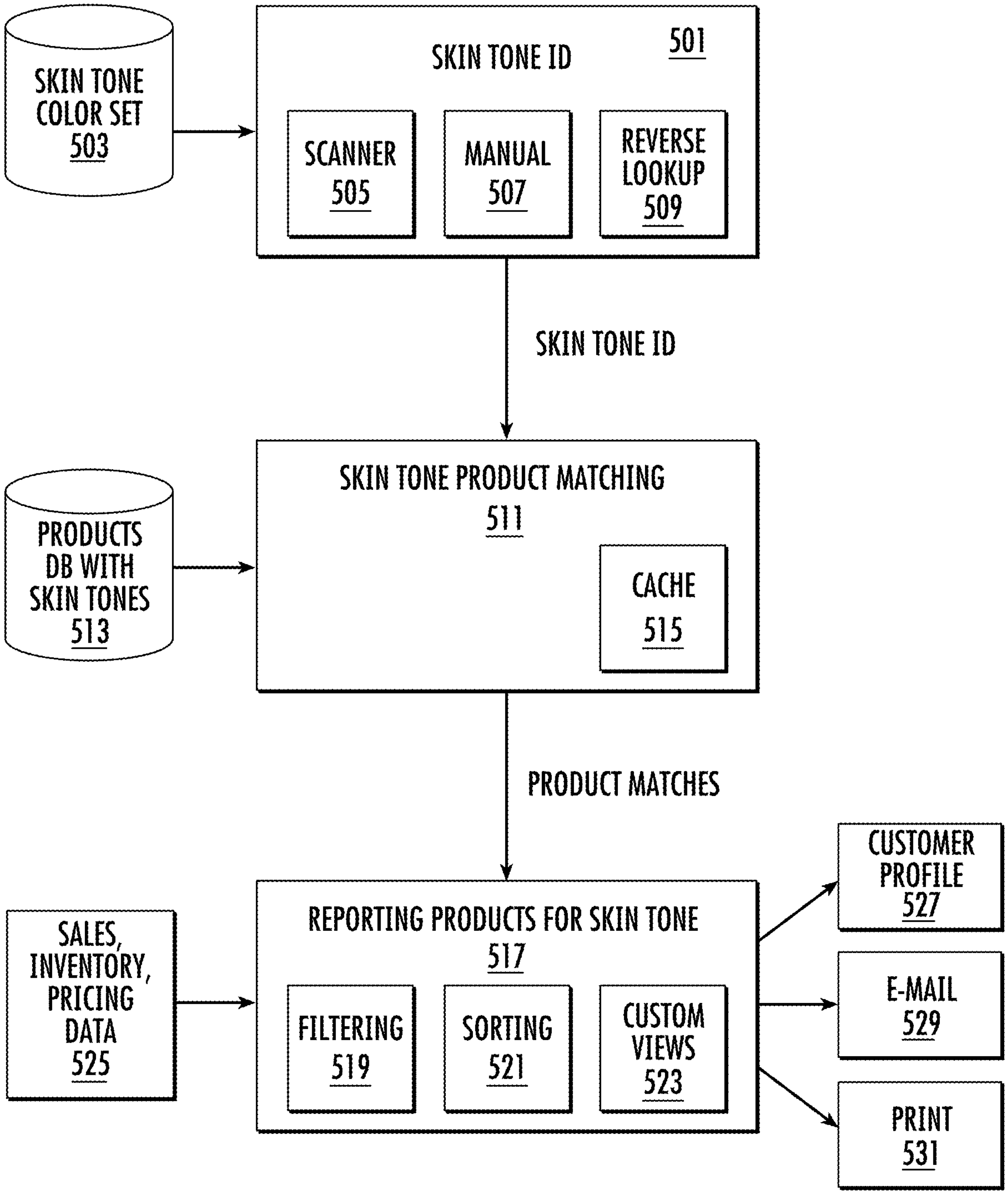
FIG. 5 shows a front end of the system for product matching based on skin tone.

FIG. 4 shows a back end of a system for product matching based on skin tone. FIG. 5 shows a front end of the system for product matching based on skin tone. A specific implementation of the system is Sephora's Color IQ system. All public published content by Sephora, including Web pages available at www.sephora.com, to the filing date of this patent application is incorporated by reference along with all other cited references in this application. This published content includes Web site pages, user guides and manuals, white papers, and other on-line and paper publications and documentation (including material related to Sephora's Color IQ system).

Human beings come in many different skin tones. For products such as cosmetics that are individualized to a person's skin tone, it is often a difficult and time consuming task to select a product that is the correct color match to a person's skin tone. Some examples of cosmetic products for which color match to skin tone is important includes foundation and tinted moisturizers.

A system allows customers to more easily find products matching their skin tone. In an implementation, a handheld scanning device allows a product specialist (e.g., salesperson or Sephora cast member) to digitally scan various spots on a customer's face. For example, three spots in different locations are scanned. The color capture technology then assigns each person a skin-tone number (e.g., Pantone SkinTone Guide in Pantone's Pantone Matching System or PMS color space). The skin-tone number is then entered into a software program executing on a tablet computer (e.g., Apple ipad app). The program determines and outputs a listing of foundations and other products that are the closest match for the customer's skin tone. As can be appreciated, this system reduces (or eliminates) the amount of time customers need to find the products matching their skin tone.

In an implementation, the system includes a kiosk for a retail store. This kiosk includes signage regarding the skin tone matching system, a tablet computer (e.g., Apple iPad), and a scanner device. The tablet computer is tethered to the kiosk, such as mounted in a tablet stand attached to the kiosk. The scanner device has no cables and can have a holster or other holder. There can be two or more tablet computers in the kiosk, and a corresponding number of scanner devices and holsters.

Referring to the back end in FIG. 4, the system determines and creates a skin tone color set which the products will be mapped to. This color set is determined based on taking a sample population of people 401 that represent the range of skin tones. For example, the colors can be developed to present the best color match when evaluated under D65 (Daylight 6500K) lighting. This population sample can include people of different ethnicities and geographical areas. This population sample is analyzed to gather skin tone colors 403. Based on the analysis, a skin tone color set is created to represent the range of skin tones in the general public 405. This skin tone color set includes a number of different skin tone colors, each referred to by skin tone identifier or skin tone ID. This skin tone color set can be stored in the database 407 or other data structure (e.g., table, array, file, string, or other).

In a specific implementation, the skin tone color set includes 110 different skin tones, but a skin tone color set can include any number of skin tone colors, more or less than 110. Generally, for a greater the number of skin tones, products can be more finely customized to a person's skin tone.

The skin tone color set can be a proprietary color space such as the Pantone SkinTone Guide, which has 110 skin tone shades (e.g., numbered from 1Y01 SP to 4R15 SP), the Munsell color system (color specified using hue, lightness, and chroma), or other color space. The system can use a color space that includes only colors corresponding to skin tones found in the general population, so that the color space is simplified and reduced to only existing skin tone colors. This can allows the color space to specialize on skin tones, instead of needing to represent all the possible colors found in the world. For example, the color space can be based on undertones and darkness, two factors that affect a person's skin tone.

For more information on Pantone, see the www.pantone-.com, which is incorporated by reference along with all published matter related to the Pantone SkinTone Guide. All references cited in U.S. provisional patent application 61/826,488, filed May 22, 2013, (including appendixes) and this application are incorporated by reference. U.S. patent application Ser. Nos. 13/924,549, 13/924,550, 13/924,551, and 13/924,552, filed Jun. 22, 2013, are incorporated by reference.

Although the Pantone color space is specifically described in this application, one having ordinary skill in the art would recognize than a skin tone matching system of the invention can use any other color space, proprietary, public, or open source. For example, a skin tone color space (not using Pantone) can be independently developed for a cosmetics skin tone color matching system of the invention. Some additional example color spaces that the system can use include sRGB (standard Red, Green and Blue), Adobe RGB, HTML, CMYK (Cyan, Magenta, Yellow, and Key), Lab, and XYZ values.

The skin tone color set can be referred to as a unified, uniform, or reference skin tone color set against which products are mapped. A database of products across different manufacturers 411 is mapped to the reference skin tone color set. As an example, there can be manufacturers A, B, and C that manufacture foundation using their own color schemes and names. Some examples of cosmetics manufacturers include Amazing Cosmetics, bareMinerals, Clinique, Dior, Korres, and many others. These manufacturers produce a variety of products. These products are further divided by these manufacturers and their products will often use proprietary labeling and naming for their products. For example, manufacturer A may call their foundation colors called cocoa, toffee, honey, and sand. Manufacturer B may use different names such as rich coffee, southern tan, warm sunset, and light sunset.

The system evaluates and maps the products of the different products 409, usually having different color names, of the different manufacturers to the reference skin tone color set. Each product is evaluated in a laboratory to determine a primary and secondary skin tone match. These skin tone matches indicate the skin tone which the product is compatible with colorwise. For some products, they may be suitable for only a single skin tone color match. Other products, such as a tinted moisturizer may match a more than one skin tone. A number of skin tones can be listed in the secondary match. This can be defined as a range of possible values or values otherwise chosen from a skin tone color set. A system can include any number of skin tone matches for a product, one, two, three, four, five, or more. The laboratory skin tone matches can be verified manually by applying the product on a person. This verification of the laboratory results is optional.

Then, for each evaluated product, the skin tone identifier or identifiers (in the reference color set) is added into a products database with skin tone 413. In addition to skin tone information, the products database can include other information about each product. Some information this database can include are the brand name of a product, the product name, a shade name, a product picture, and its skin tone identifier.

The reference skin tone color set and products database with skin tones are used by the front end of the system. Referring to the front end in FIG. 5, to use the system, the particular skin tone of a customer in the skin tone color set is determined 501 and matched to an entry in the skin tone color set 503. As described above, this can be done by using a color scanner to scan various points on the person's face or other area of the body where they want to apply a cosmetic product. Then the scanner displays a skin tone identifier.

In addition to scanning using an electronic scanner device, the skin tone of the customer can be determined manually 507 or by reverse lookup 509. For manual entry 507, a computer can display a color swatches of the skin tone color set (e.g., an array of skin tone colors), or there can be printed color swatches. These color swatches can be compared against a person's face to determine visually which skin tone color in the color set is closest to the customer's. Then the identifier for the skin tone color is determined. This skin tone identifier, determined manually, can be used to find other products suitable for the customer.

For reverse lookup 509, the customer may be using a particular product. That product can be entered into the system, and a reverse lookup is performed using the product database with skin tone, to determine its associated skin tone identifier. This skin tone identifier, determined by reverse lookup, can be used to find other products suitable for the customer.

Further, the customer may have been previously scanned by the system, and information saved in the customer's profile (such as part of a customer loyalty or reward program such as Sephora's Beauty Insider). In a further implementation, the skin tone information saved in the customer's profile can be retrieved by the system.

After the skin tone identifier is determined, a skin tone product matching component 511 of the system determines products that match or are compatible with the determined skin tone identifier. This component accesses the products database with skin tones 513 and finds the products having determined skin tone identifier as a primary or secondary match. The result is one or more products, generally a subset of products in the products database, which match the customer's skin tone.

In an implementation, the skin tone product matching component includes a software application executing on a tablet device such as an Apple iPad. The tablet device includes a cache 515 (e.g., nonvolatile memory) which stores information such as the products database with skin tone. Storing the products database with skin tone in cache on the tablet generally increases the responsiveness of the device since queries do not need to go over a network connection, reduces the amount of network traffic, and ensures the device will be usable even if the network connection was unavailable.

The skin tone product matching software, information in the cache, and other software of the tablet can be updated periodically. For example, updates can occur daily automatically, outside of business hours for the retail store (such as 3 a.m. in the morning), so that the device and software is already up-to-date at the start of the business day (e.g., 9 a.m. when the shopping mall opens). Also, the software can be updated manually from the back end (e.g., system administrator pushing out an important update) or front end (e.g., software user requesting updates).

After the products matching the skin tone are determined, this information can be passed to a reporting component 517. Like the product matching component, the reporting component can be software application executing on a tablet device, and may be integrated with the skin tone product matching component, or may be a separate component (e.g., such as a browser or other viewer). With this component, the user (e.g., salesperson or customer) can view the product matches. All the product matches can be viewed, or the user can filter 519, sort 521, or have a custom view 523 of the product matches. For example, the customer can browse their product matches one or more of these categories: brand, formulation (e.g., cream or powder), coverage, finish, radiance, skin type (e.g., dry skin or oily skin), ingredients, or sun protection factor (or SPF or PABA free).

In a specific implementation, the system can also sort the products based on certain criteria. For example, the system can have access to sales, inventory, or pricing data 525, which may be accessible via a network. Then products listed higher in the list may be those that are inventory in that particular retail store, while others which are out of stock or available on-line only are listed lower in the list.

Further, the system can allow a factor for a cosmetic product more weight than others, when displaying it to a customer, so that it appears with more prominence to the customer. In an implementation, the system uses a best seller rating to rate some products above others. The reporting products module also can retrieve information from the sales, inventory, and pricing data 525, so that a customer or sales representative can retrieve relevant information about each product.

The product matches can be saved for later use by the customer. For example, the matches can be saved to the customer's profile 527, e-mailed to the customer 529, or printed for customer 531 (e.g., using printer in the store). For example, the customer will be able to retrieve the product listing when accessing their customer profile on-line.

Since network connections might be intermittent or down in a retail environment, when the requested output is not immediately transmitted (e.g., via e-mail), the reporting component can save (e.g., place in queue) its product matches or selected products on the device for later transmission when the network becomes available again. For example, the user may wish to e-mail the products listing to an e-mail account, but the network is not available. The user can click the e-mail button, and continue using the application with other customers. Then when the network connection becomes available, the e-mail and another other queued up operations that require network connectivity, will be processed. This may occur any amount of time (e.g., 5 minutes, 1 hour, 7 hours, and so forth).

In an implementation, the system is inventory aware. This means that in stock inventory levels (e.g., on hand at a given store location, available on-line) affects what is shown in the reporting products module. For example, the system can use a special indication (e.g., icon, highlighting, higher listing in a sorted product list) to show that a product is available.

In another implementation, the system includes assortment awareness. The application should identify product matches that are not in the store assortment, but are carried online, and be able to designate those products as such (e.g., carried online and not in that specific store).

Figure 6:
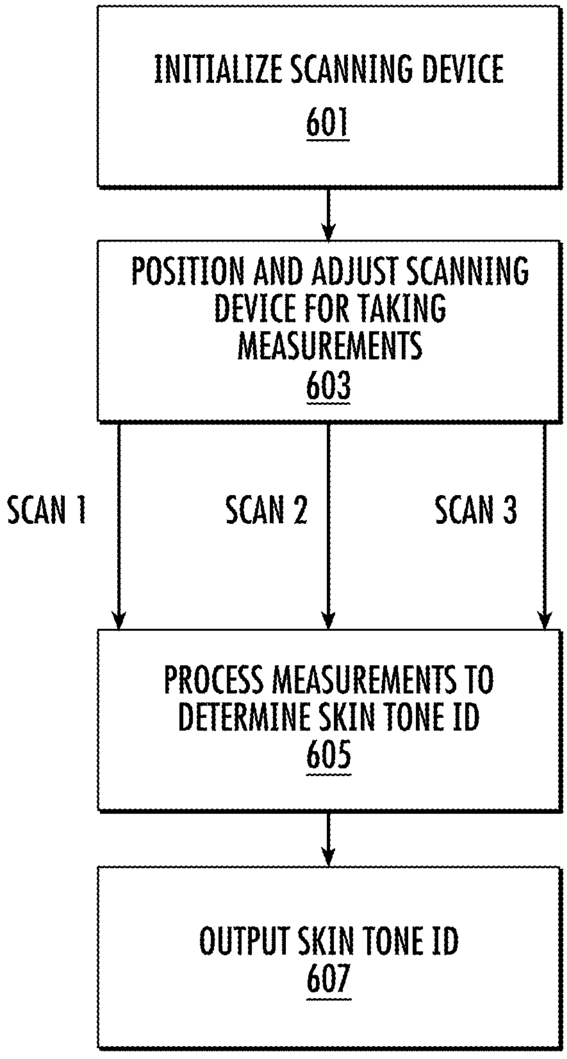
FIG. 6 shows a flow of using a scanning device to determine a person's skin tone.

FIG. 6 shows a flow of using a scanning device to determine a person's skin tone. As discussed, the system can include a scanning device (which may be optional) to determine the skin tone identifier for a customer.

In a specific implementation, the scanning device is handheld and has a rechargeable internal battery. The rechargeable battery can last a typical work day and is recharged once daily. The device is wireless. A bottom side of the device has one or more elements (e.g., photosensitive element) and lighting sources (e.g., 32 LEDs) used to uniformly illuminate the skin. A top or front side of the device includes a display (e.g., liquid crystal display (LCD), organic light emitting diode (OLED) display, or other flat panel display technology) that is used to display the determined color skin tone identifier (e.g., Color IQ number).

In comparison, traditional cameras uses ambient light to provide illumination to make a scan, but this can cause huge pigment variables that distort the scan's color. The system can measure pigment in pitch darkness, does not require ambient lighting for precision matching. Also, a scanning portion of the scanning device can applied closely to a customer's skin, to reduce or block out ambient light. Other methods can also be used to minimize ambient lighting that may cause an erroneous reading by the scanning device. In an implementation, the scanning device includes a light source (e.g., light-emitting diodes, incandescent light, or fluorescent light) that is powered on when a scan is taken. In other implementations, the system includes a shade or other physical device to reduce external lighting when taking a scan.

Referring to FIG. 6, the system initializes a scanning device of the system 601. Initializing can include cleaning, calibrating the scanning device (e.g., resetting a color space of the device), updating the device to new drivers or firmware, inspecting the device for damage, or other steps.

The scanning device is positioned and adjusted to take scans (or measurements) from the customer 603. The scanning device will capture a reading of the skin tone of the customer at various locations. The system works best when taking into consideration and avoiding areas with freckles, rosacea, blemishes, and hyper-pigmentation that may affect the scans. The scanning device can take scans from three areas of the customer.

Although three scans are used in an implementation, in other implementations, there can be fewer than three scans or more than three scans. For example, a system can use one, two, four, five, six, seven, or more scans to determine a customer's skin tone identifier. Some example areas of the customer to take a scan include: jaw line; cheek; in between eyebrows; behind the ear; neck; inside of forearm; forehead; and other areas of the customer.

The system processes the three scans to determine a skin tone identifier 605. For example, the skin tone identifier is displayed or output on a display of the scanner device. The device averages the three scanned values to determine a single skin tone identifier. In a specific implementation, the skin tone identifier is represented as a four digit alphanumeric code.

The skin tone identifier includes information on the hue or undertone of the skin, as well as the tone or lightness and darkness of the skin. In an implementation, the system uses a four character system to represent a skin tone identifier. For example, for the Pantone SkinTone system, the skin tone identifier of 1Y01, the first two characters represent a color (Y corresponds to yellow) and how strongly hued the customer is (1 corresponds to a very light hue). The second two characters represent the tone (01 corresponds to a light tone). In another example, 5Y07 would mean that skin tone is the most yellow (5Y) for that mid range depth (07). Skin tone 1Y07 would be the same depth in skin but the saturation in color is the least yellow and closer to neutral.

In an implementation, undertones can be represented using other metrics. For example, the system can rate undertones by: coolness (e.g., pink, red or bluish undertones); warmness (e.g., yellow or golden undertones); neutral (e.g., a mix of warm and cool undertones). Olive (e.g., similar to neutral as being a mix of warm and cool undertones) can also be included in this undertone rating system.

The system outputs the skin tone identifier 607. The system can display the skin tone identifier on a screen of the scanning device. In another implementation, the skin tone identifier can be electronically transferred to another device or computer, such as by wireless or network transmission.

Figure 7:
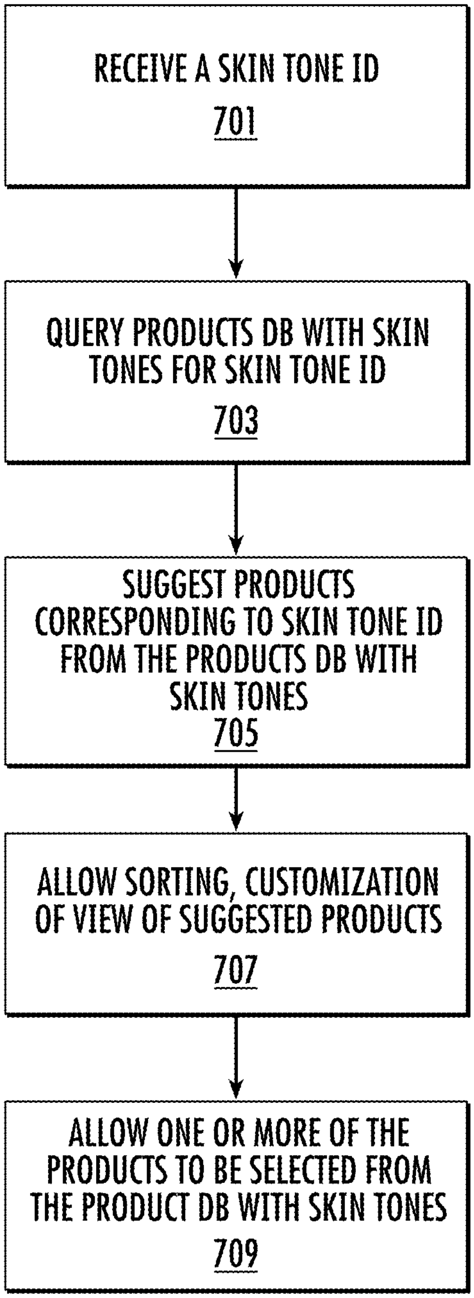
FIG. 7 shows a flow for a user of the system.

FIG. 7 shows a flow for a user (e.g., salesperson or customer) at the front end of the system. For example, this flow can be implemented on a touch-screen enabled computer, tablet, or other computing device.

When the customer uses the system, the customer enters in their skin tone identifier (e.g., four digit alphanumeric code) 701. The system queries the products database with skin tones for the products associated with the determined skin tone identifier 703. As discussed above, the product database can be stored on the computing device or accessible over a network. The system presents the customer with suggested products corresponding to the skin tone identifier 705. These products are those that are suitable for the customer, based on the skin tone identifier. The system allows the user to perform sorting and customization of the views 707. The customer can easily compare products, such as what features are present with the suggested products. This lets the customer quickly learn about their suggested products. The system allows the customer to select one or more products from their suggested products 709. This can include adding the products into a virtual shopping cart, printing the product listing, e-mailing their choices, or saving their selections for later purchase or consideration.

Figure 8:
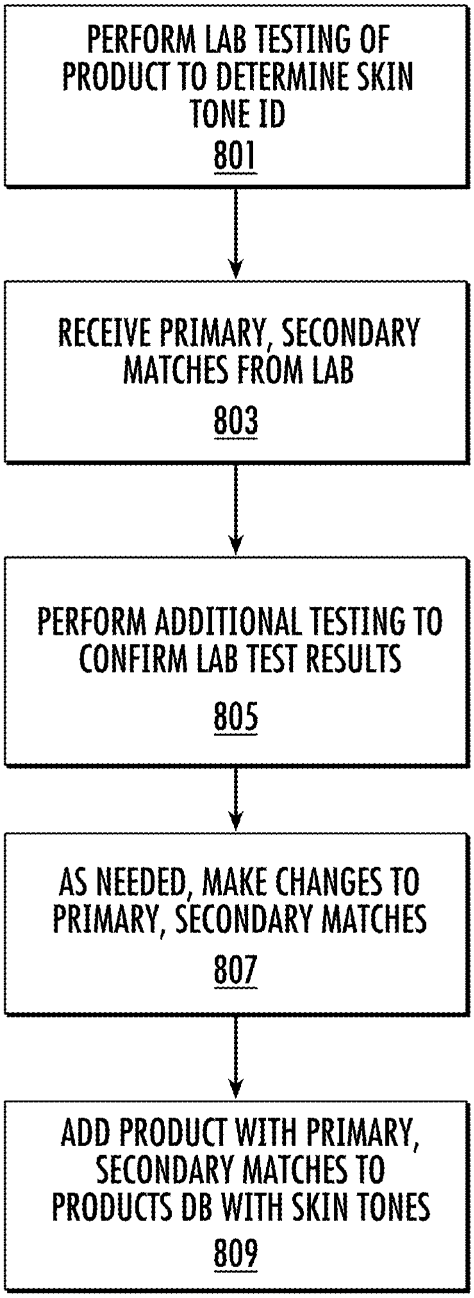
FIG. 8 shows a flow of evaluating products in an implementation of the system.

FIG. 8 shows a flow of evaluating products in an implementation of the system. The system performs lab testing of product to determine the corresponding skin tone identifier of a product 801. The system receives the information on the primary and secondary matches (e.g., which skin tone identifiers the product corresponds to) 803. The system performs additional testing to confirm the initial results 805. The system modifies the initial results as necessary 807. The product is stored in a product database with skin tones, along with its primary and secondary matches 809.

In an implementation, the system allows adjusting their selections (or matches). For example, after the system has determined a primary match, a customer may choose to adjust what products are suggested to them. Some of the adjustments a customer can make for are to make their matches redder, yellower, darker, lighter. For example, a customer may think that the suggested products (e.g., primary match) are too dark or light, selected a wrong shade or color base, or believes that their skin tone will change soon (e.g., due to tanning in the summer, staying indoors for the winter, or other reasons where the customer's skin tone may change).

FIG. 9 shows a skin tone color set in an implementation of the system. Skin tone shades are organized visually in the grid with lighter to darker on the vertical 901 (lighter at the top) and redder to yellower on the horizontal (redder to the left) 903 to show the relationship between shades. For example, for a skin tone identifier value in the grid, the vertical axis can be referred to as measuring the darkness for the skin tone identifier, while the horizontal axis can be referred to as measuring the undertone for the skin tone identifier.

The redness and yellowness have numerical values from 1-5, where 1 is the least amount of red or yellow and 5 is the most amount of red or yellow. Red and yellow extend left and right in the charge. Darkness is numbered 1 to 15, 1 being the lightest and 15 being the darkest. Lightness or darkness extends from top to bottom of the chart.

Figure 10:
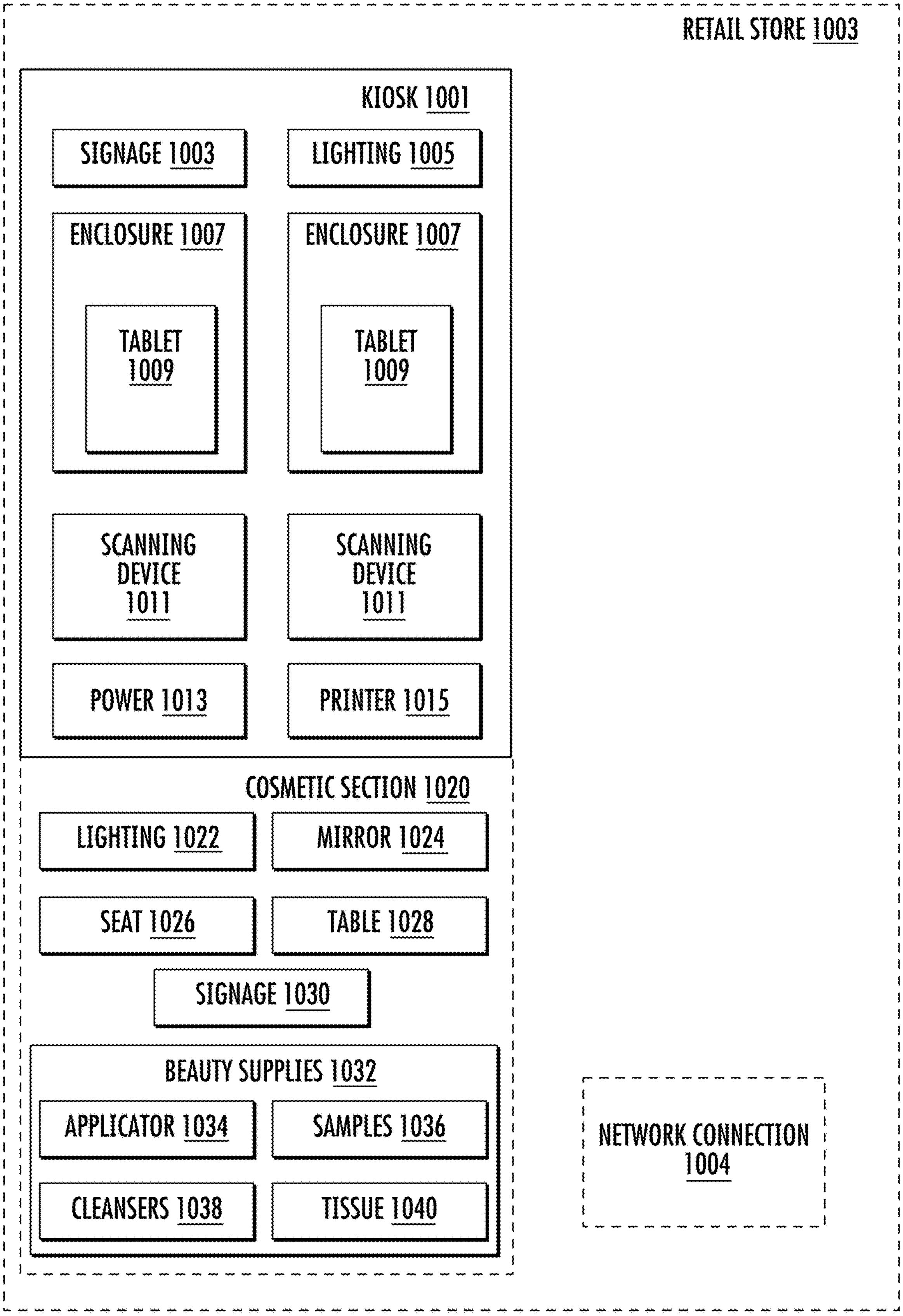
FIG. 10 shows a block diagram of a kiosk of the system.

FIG. 10 shows a block diagram of a kiosk or station of the system. The kiosk (or station) 1001 is part of or located within a larger retail store 1003 that can have more than one kiosk. The retail store can include multiple retailers selling a variety of products, such as in a large department store. The retail store can also include a network connection (e.g., a wireless network connection) 1004. The kiosk includes signage 1003 including information regarding how the system works. For example, the system can describe the benefits of the system, how the system allows selection of proper cosmetic products for a customer, and a brief summary of a methodology of the system. In another implementation, the signage includes brochures or other informational materials that explains the system.

The kiosk can have a counter (or horizontal surface) and a vertical surface (or wall). There may be chairs. Typically kiosk is a stationary, without wheels, at fixed at a location in the retail store. However, in other implementation, the kiosk can include wheels so it can be moved to another location as needed, and the wheels locked to prevent from rolling. The kiosk has a cord that is connected to an electrical outlet to provide power for the components of the kiosk. This cord is typically hidden beneath an enclosure of the booth, to prevent customers tripping over the cord.

In a specific implementation, the kiosk or station can include two tablet computers 1009 in enclosures 1007. In other implementation, the kiosk or station can include any number of tablet computers, more or fewer than 2, such as 1, 3, 4, 5, 6, 7, 8, or more. When a particular store has higher levels of customer traffic, the kiosk can have greater number of tablets to handle the anticipated demand. Also, to increase the number of devices, there may be multiple kiosks in a store.

The enclosures are designed to hold the tablet and protect the tablet (e.g., from falling onto the floor, theft, or other hazards). The enclosures can also include a power mechanism, so that the tablet device can be charged while the device is in the enclosure. The tablet can be connected on the wireless network of the retail store, if one is available.

Although tablet computers are specifically discussed in this application. It should be understood that other types computing devices may be used instead, such as desktop computers, notebook computers, smartphones, point of sale (POS) devices, and many others.

In an implementation, the enclosure includes an arm attached to the kiosk. The arm holds the enclosure and tablet viewing surface at a specific angle with respect to the ground surface. For example, with the tablet viewing screen facing upwards, the tablet can be held at approximately 15, 20, 25, 30, 35, 40, 45, or more degrees with respect to the ground. The tablet is also held above the ground at a specific height. For example, the tablet can be held at 76, 89, 102, 115, 128, 140, or more centimeters above the ground. Generally, as the height of the tablet increases, the tablet is held at a lower angle (lower number of degrees) with respect to the ground. This allows the tablet to be used by customers in a variety of positions (e.g., standing, sitting in a chair, sitting in a stool, or other position) while in a comfortable position.

In another implementation, the tablet angle is an adjustable angle, so that customers can adjust the angle when using the tablet. This can be done with the tablet attached to the kiosk or temporarily removed from the kiosk. For example, the tablet is removable from the kiosk while still in the enclosure. A cable or other device can tether the tablet to the kiosk and prevent it from being taken away too far from the kiosk.

In a specific implementation, the kiosk includes two scanning devices 1011. The scanning devices are handheld, and can be used wirelessly. Other implementations of the kiosk can include more or fewer scanning devices. In other implementation, the kiosk or station can include any number of scanning devices, more or fewer than 2, such as 1, 3, 4, 5, 6, 7, 8, or more. Typically there are an equal number of scanning devices to the number of tablets. However in some implementations, there are fewer scanning device than tablets, such as two tablets and one scanner, three tablets and two scanners, four tablets and two scanners, or other combinations. In other implementations, there are more scanning device than tablets, such as two tablets and three scanners, three tablets and six scanners, four tablets and five scanners, or other combinations.

By adding more tablets or scanning devices, more customers can interact with the kiosk at a given time. By removing tablets or scanning devices, a smaller space for the kiosk is necessary, as well as less maintenance and energy requirements.

The kiosk also includes a power receptacle 1013. The power receptacle includes an electrical connection so that the tablet or scanning device can be powered or recharged at the kiosk. The kiosk optionally includes a printer 1015. The printer can print relevant information for the customer, such as their skin tone identifier or products they may be interested in. The kiosk includes lighting 1005 that illuminates portions of the kiosk. This can include illuminating the signage and tablet areas.

The kiosk can be included with an optional cosmetic section 1020. With this section, a salesperson or other professional can assist a customer in trying the cosmetic products suggested by the system in store, before purchase. This section includes cosmetic products, materials, and related items for the customer's trial experience. This includes lighting 1022, mirror 1024, and seat 1026. A table or counter 1028 is also included. The table can be specially designed with drawers of depressions for holding samples and other cosmetic products. The table can include an area to place beauty supplies currently being used. The cosmetic section includes signage 1030 advertising the specific retailer associated with the kiosk (e.g., the assignee Sephora).

Cosmetic section 1020 also includes beauty supplies 1032. Some example of these supplies include applicators 1034 (e.g., brushes, swabs, or other devices used to apply cosmetic products), cosmetic samples 1036 such as store trial versions of products, cleansers 1038 (e.g., toners, gels, soaps, wipes, or other cleansers), and tissues 1040.

In an implementation, the kiosk is customized to a geographical location of the kiosk. This means that depending on where the kiosk is installed, the information on the kiosk is presented in the local language. The system can support French, Chinese, Korean, Japanese, Arabic, Hindi, Russian, German, Italian, or other languages. Signage, the tablet application, and other parts of the systems described can be adapted to use localized languages.

Figure 13:
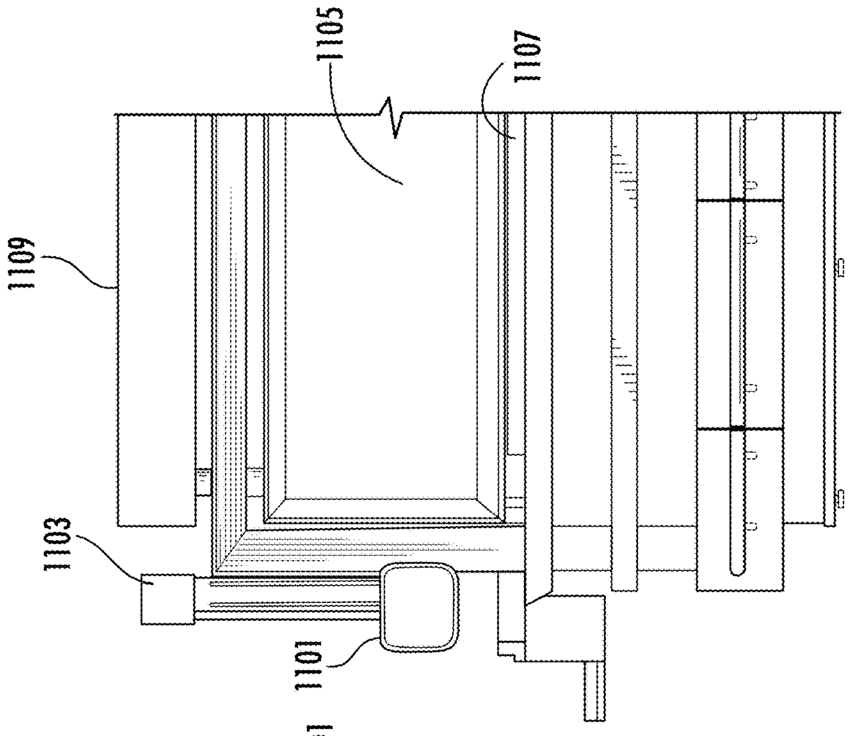
FIG. 13 shows a side view of the embodiment of the kiosk of the system.
Figure 12:
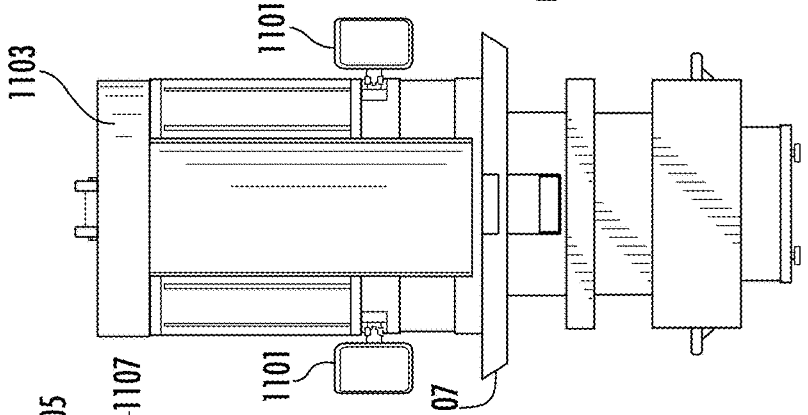
FIG. 12 shows a front view of the embodiment of the kiosk of the system.
Figure 11:
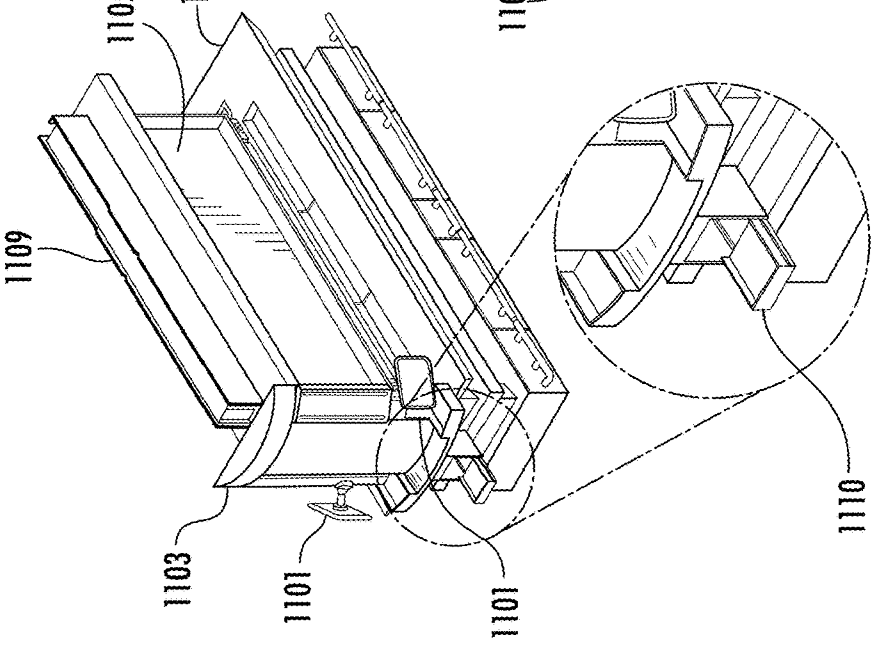
FIG. 11 shows a perspective view of an embodiment of a kiosk of the system.

FIG. 11 shows a perspective view of an embodiment of a kiosk of the system. FIG. 12 shows a front view of the embodiment of the kiosk of the system. FIG. 13 shows a side view of the embodiment of the kiosk of the system. In this embodiment of the kiosk, the kiosk is an endcap unit to a cosmetic section. The endcap unit can be inserted to an end of the cosmetic section and secured (e.g., using bolts) onto the cosmetic section. The endcap includes at least one tablet 1101 (e.g., two tablets 1101) and signage 1103.

The cosmetic section includes a mirror 1105 and counter 1107. The mirror does not necessary extend the entire length of the counter, but enough to allow users to see themselves with their products. A base of the endcap partially rests on top of the counter. This can help support the weight of the endcap unit when used with the cosmetic section. While the signage for the cosmetic section includes a signage 1109 specific to a retailer of the kiosk (e.g., Sephora's "Beauty Studio"), the signage of the endcap unit 1103 includes signage specific to the system (e.g., "Sephora Matching Color IQ"). The endcap includes a compartment 1110. This compartment can be used to hold items for use with the system, such as scanning devices of the system when they are not in use.

Figure 14:
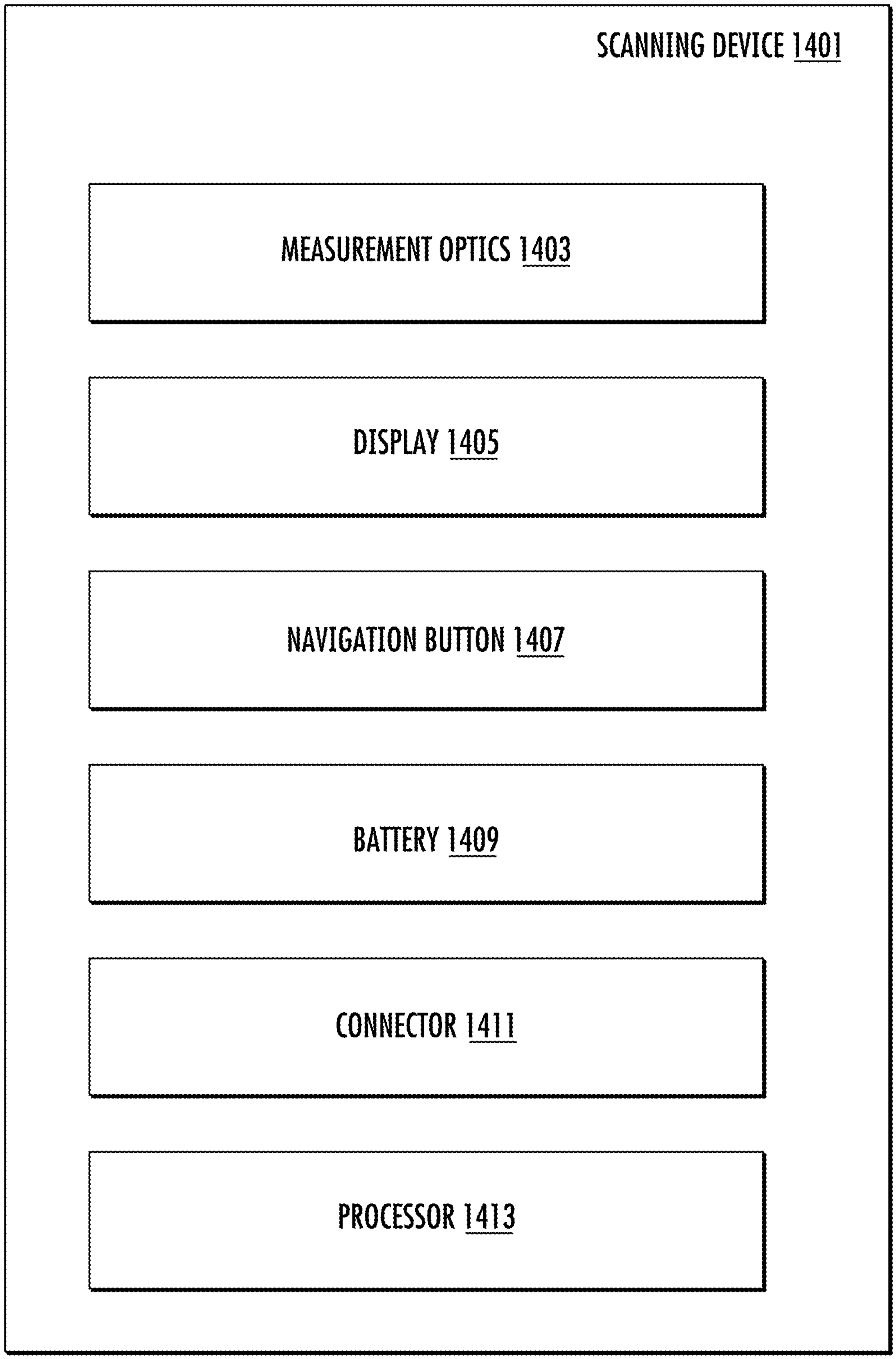
FIG. 14 shows a block diagram of a scanning device of the system.

FIG. 14 shows a block diagram of a scanning device 1401 of the system. The scanning device includes measurement optics 1403. The measurement optics are placed on the skin surface of a user to take the scan of a sample area. More fragile portions of the measurement optics (e.g., lighting elements, photosensitive elements, or other elements) can be prevented from making direct contact with the user's skin. For example, these fragile portions can be in a module that is recessed within the scanning device to prevent direct contact with skin when in use. Transparent plastic or other material can be used to make direct contact with the user, while still allowing light in and out from other elements of the measurement optics.

The measurement optics can use a variety of methods to determine a skin color tone of the sample area. In one method, the system uses lights of different colors or different wavelengths to illuminate the sample area. With each wavelength, the measurement optics takes a picture of the sample area. Each picture can include the sample area illuminated by one specific wavelength. The measurement optics can operate on a wide spectrum of wavelengths. This can include any wavelengths from the infrared to the ultraviolet range. In an implementation, a scanning device of the system takes approximately 1.8 seconds to complete a scan for an area. The device produces 27 photographs in black and white using 8 different visible light emitting diode bands and 1 ultraviolet band. The scanning system can use sensors sensitive to red, green, and blue (RGB) color wavelengths. In another implementation, the scanning system can use sensors sensitive to cyan, magenta, yellow, and key (black) or CMYK color wavelengths.

In an implementation, the system uses light of multiple colors when taking images. This can create, for example, white light or other color from a combination of different colored light emitting elements.

The scanning device can include a display 1405 and navigation buttons 1407. The display can present relevant information about the device status or operation status. The display can alert when the device is at low power, needs to be updated (e.g., firmware, software, color space, or other updates), needs to be recalibrated (e.g., to reset the color space to white or other reference point), previous results for skin tone identifiers, or other system alerts. The navigation buttons allow the user to select items shown on the display. For example, the display can display an image of the sample area (e.g., in color) being scanned. Using the navigation button, the user can select with greater specificity which portion of the sample area is relevant. This can be useful, for example, when the sample area includes a blemish that may not accurately reflect a person's overall skin tone. An area not affected by the blemish can be selected in the sample area by using the navigation buttons.

The scanning device can also include a battery 1409. The battery supplies enough energy for multiple scans, but can be charged when connected to a power source at a connector 1411. For example, the scanning device should hold enough charge to last a day of regular use (e.g., 7 to 10 hours) before needing to be charged. The connector mechanism can be part of an established standard (e.g., USB charging adapter, mini universal serial bus, micro universal serial bus, or other standard) or a proprietary standard. The connector can also be adopted to transfer information (e.g., updates, scanned information, or other information) to and from the scanning device. For example, the battery can be a lithium ion, lithium polymer, nickel metal hydride, nickel cadmium, or other rechargeable battery chemistry.

In a specific implementation, the kiosk includes a charging holster or tray (which may be hidden in a cabinet) for the scanner. At the end of the day, the scanning device is placed in the holster for charging. The holster can connect via a wire or cable to a charging the battery of the scanning device. In an implementation, the scanning device is charged via wireless charging by placing the area of an inductive charger. Then the battery is charged via inductive charging. In another implementation, the scanning device has a removable battery pack. The battery pack is removed and placed in a charging unit for the battery, while another battery pack that is already charged is placed into the scanning unit. Typically the battery pack is kept in the charging unit until needed.

The scanning device includes a processor 1413. The processor can be used to process information determined by the measurement optics. In an implementation, the processor receives information of scans from the measurement optics (e.g., two, three, four, or more scans) and processes (or maps, averages, blends, or mixes) the information to determine a single color value. This color value maps to a single skin tone identifier in the skin tone color space. This information can be displayed on the display 1405 of the scanning device. The skin tone identifier displayed value in display 1405 can be entered (e.g., manually entered) into tablet device by a user.

In further implementations, the scanning device may be connected to the tablet device so that the skin tone identifier is automatically available to the tablet device. This can be via a directly wireless connection such as Wi-Fi or other wireless connectivity technology or a wired connection such as a cable, or any combination of these.

For example, the scanning device can be connected wirelessly to a network (e.g., Ethernet), and the tablet or other computing device is connected wirelessly to the same network. In another example, the scanning device can be connected by wire to a network (e.g., Ethernet), and the tablet or other computing device is connected by wire to the same network. In another example, the scanning device can be connected wirelessly to a network (e.g., Ethernet), and the tablet or other computing device is connected by wire to the same network. In another example, the scanning device can be connected by wire to a network (e.g., Ethernet), and the tablet or other computing device is connected by wireless to the same network.

In a still further example, the scanning device can be connected by wire directly to the tablet or other computing device. In another example, the scanning device can be connected wirelessly directly to the tablet or other computing device. In another example, the scanning device can be connected wire directly to the tablet or other computing device, where the scanning device and tablet are contained within the same housing as an integrated unit.

In another implementation, the scanner can have a near field communication (NFC) or RFID capability, so that the scanner and tablet can be put near each other (e.g., being touched together) to wirelessly transmit the skin tone identifier from the scanner to the tablet. In another implementation, the scanner can display a bar code or QR code on a display of the scanner representative of a skin tone identifier. The user can use a camera of the tablet to scan the bar code or QR code to input the skin tone identifier.

Figure 15:
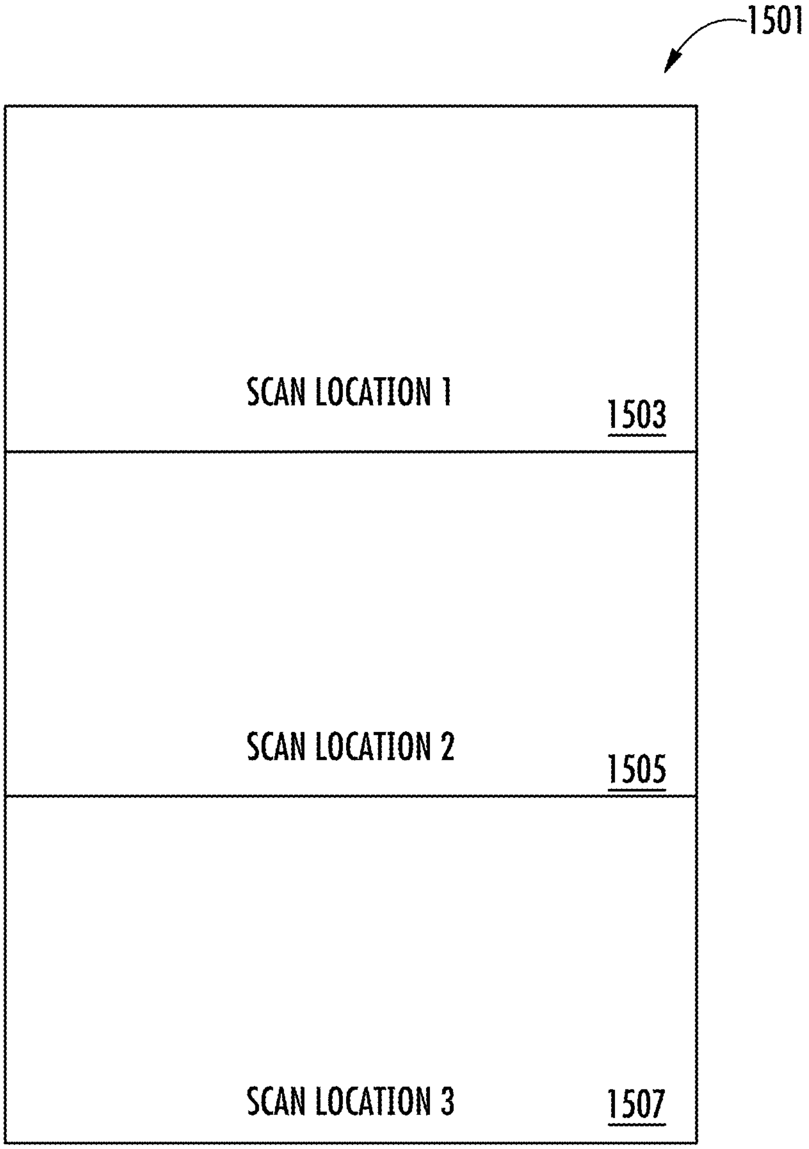
FIG. 15 shows a diagram of scanning locations for a scanning device of the system.

FIG. 15 shows a diagram of scanning locations for a scanning device of the system. A customer 1501 has multiple scans taken in various areas to determine their skin tone identifier. In an implementation of the system, this includes three areas 1503, 1505, and 1507 of the customer. The first two areas 1503 and 1505 generally correspond to areas of the customer's face, while a third area 1507 corresponds to areas below the customer's lips.

In a specific implementation, area 1503 is a region of the face above the customer's eyebrows. Area 1505 is a region of the face between the eyebrows and the chin. Area 1507 is a region of the face or body below the chin. For example, area 1503 may include the forehead. Area 1505 may include the cheekbone or cheek. Area 1507 may include the chin, neck, or upper torso.

These positions can be chosen depending on which areas are most suitable (e.g., free of freckles, rosacea, blemishes, and hyper-pigmentation that may affect the scans). These scan locations are areas where improperly chosen foundations can be visually obvious. For example, a person can have a slightly lighter shade of skin in the upper portion of their face (e.g., forehead, temple, or other areas) than their lower portion (e.g., cheek, nose, lip, or other). A proper foundation would be a color that matches both these portions of the person's face, so that the person does not have an uneven appearance when using the foundation. In another example, a foundation that matches the face but not the neck (which can be visible when wearing blouses or other clothing), can make it obvious that a person is using cosmetics improperly.

In a specific implementation, a first scan is to scan the forehead of the customer. A second scan is to scan the cheekbone of the customer. A second scan is to scan the cheekbone of the customer. A third scan is to scan the lower part of the face (e.g., a location below the lower lip, chin, neck, collar, wrist, or other).

Although in a specific implementation, three areas are scanned. In other implementations, there can be fewer or more scans. For example, a system can include only a single region to scan, such as the cheek. A system can include two scan, such as the cheek and forehead (e.g., omitting the chin region or other body part below the lips).

Other implementations of the system can include additional areas that may increase the accuracy of the color matching of the system. For example, additional scans (e.g., four, five, six, seven, or more scans) can be used to emphasize or deemphasize skin tones for the face or other areas of the customer. Additional scans can also improve the accuracy of the results of the system, by providing additional color information on the customer.

The following is an outline of a basic flow of the system in operation:

1. Remove a customer's makeup. The customer should also not have had a workout 30 minutes prior to evaluation; no chemical or harsh peels 3-6 days prior to evaluation; and not drunken more water and less caffeine prior to evaluation, since caffeine restricts blood flow, affecting the flush of skin.
2. Use a scanning device to take scans from three areas of the customer. Three photos or scan of the skin are taken, which are then averaged to find the ideal shade.
3. Read a skin tone identifier results from a display of the scanning device.
4. Enter skin tone identifier into a tablet computer.
5. View the customer's product matches.
6. Filter the customer's results to find the right foundation. For example, the system can show only liquid foundations or products that are formulated for sensitive skin.
7. Allow the customer to test their selections. A sales representative or sample can be given to the customer.
8. E-mail matches to customer. The e-mail includes a link to each product for easy purchasing.

For steps 4-6, these are performed by a tablet computer executing an application program of the system. FIGS. 16-32 show screens generated by an application program of the system. These screens provide an interactive graphical user interface (GUI) for application program. A user of the application program can interact with the application program through the graphical user interface screens. The user can be a salesperson (e.g., Sephora cast member) or customer, or other application program user.

Figure 16:
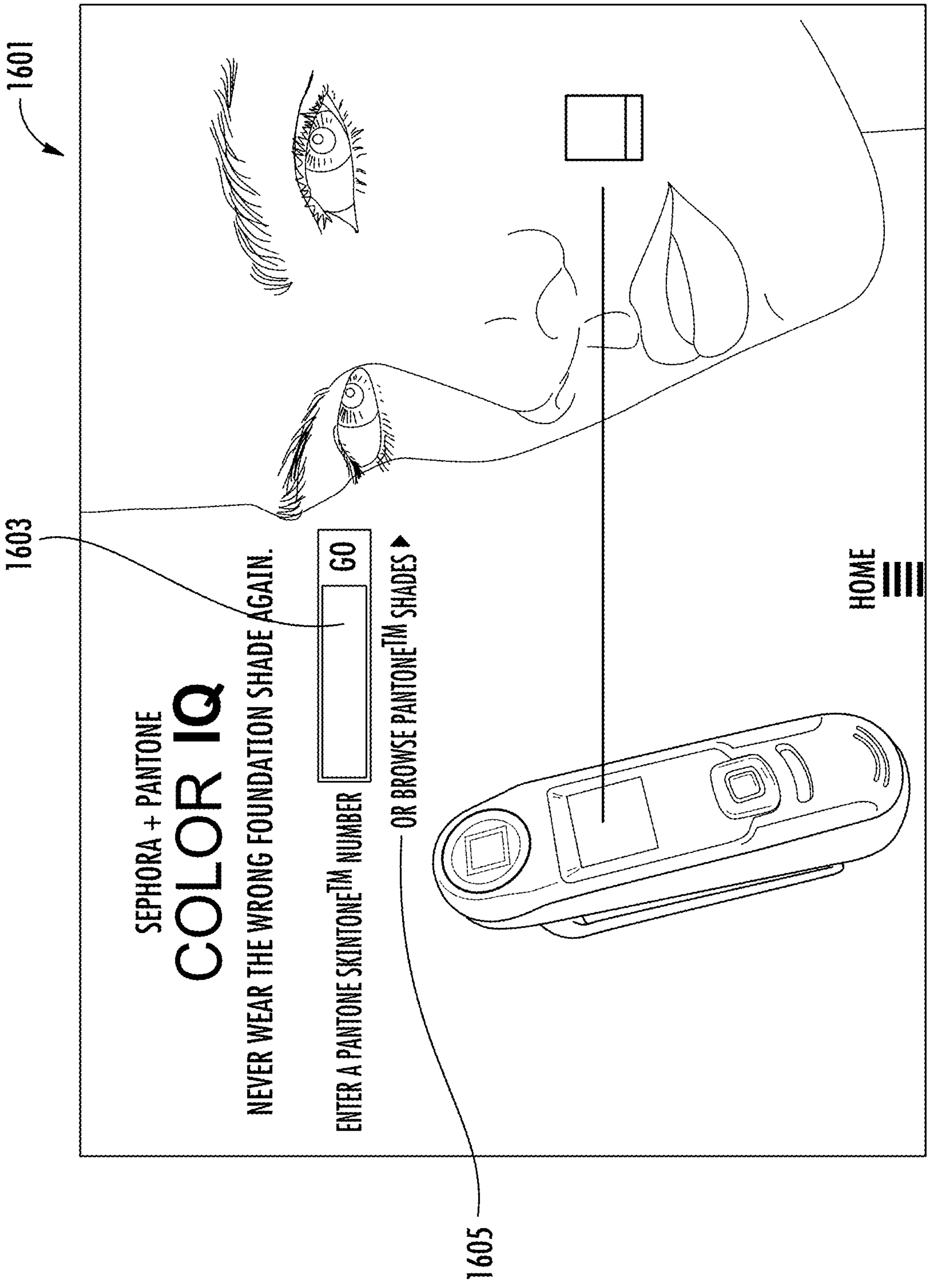
FIG. 16 shows a screen to select a product matching option.

FIG. 16 shows a screen 1601 to select a product matching option. For example, the screen is a display output from an application running on a tablet device (e.g., iPad, Android, or other tablet). This screen is a graphical user interface of the application program, and in an implementation, the screen is a touch screen.

The screen includes a box 1603 (e.g., text box) that a user can select (using their finger, stylus, or other method) and use the box to enter a skin tone identifier (e.g., "PANTONE SkinTone number"). In other implementations, box 1603 can include a drop down menu or selection box in which a menu or number of options are presented to the user from which to select from. From these options, the user can select the appropriate skin tone identifier.

From this screen, the system also allows the user to select link 1605 (represented by the text "or browse PANTONE shade") to determine their skin tone identifier. Links in the system can be represented using a variety of graphical techniques. For example, the link could be represented as an image, a button, a gesture, icons, or other interface elements.

Figure 17:
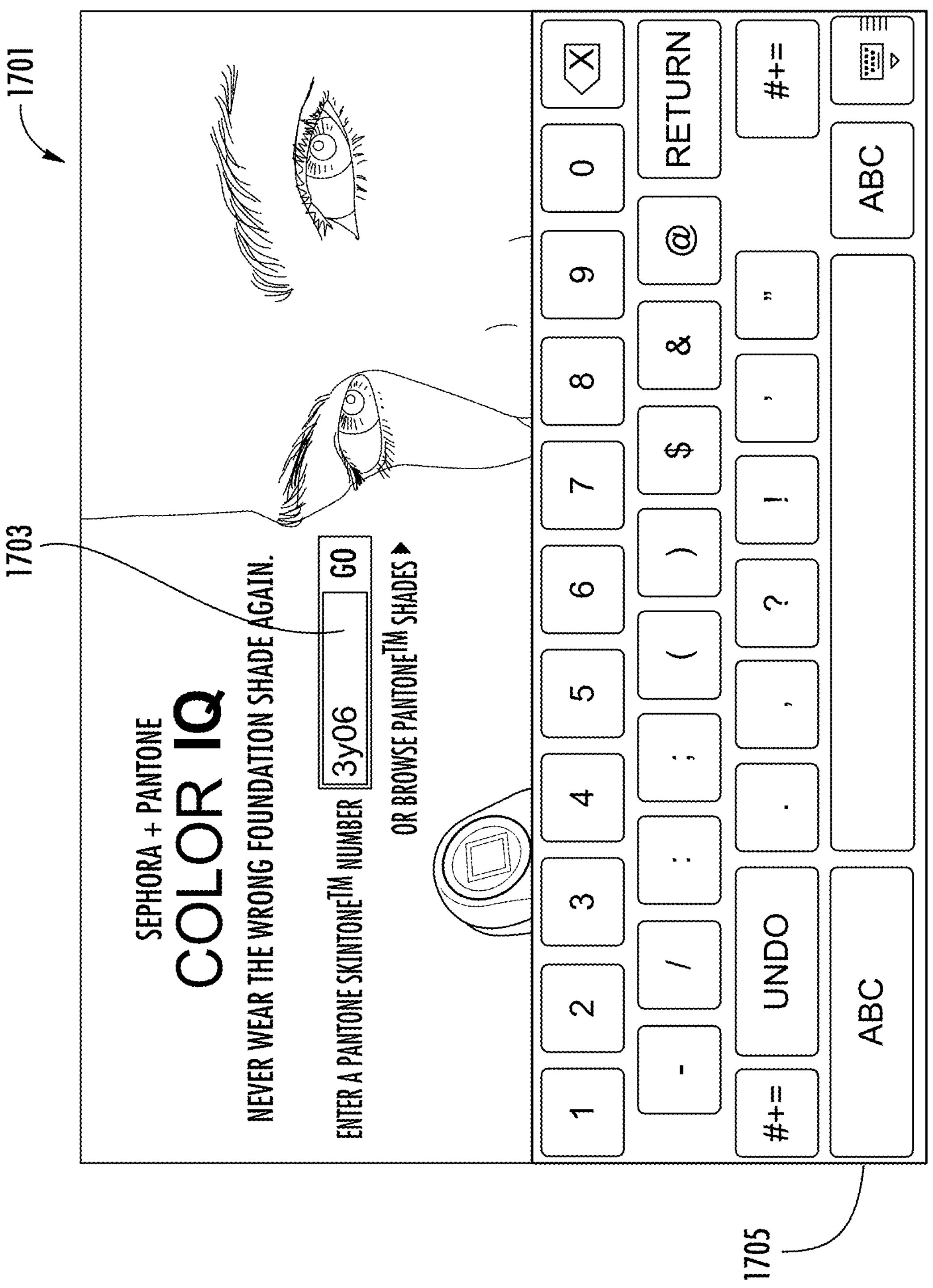
FIG. 17 shows a screen to enter a product matching option.

FIG. 17 shows a screen 1701 to enter a product matching option. When the user selects the text box 1703 (or box 1603 of screen 1601), the tablet can present virtual keyboard 1705 on the screen to allow the user to type using the keyboard, to enter text information in the box. Then the user selects "go" to input with the entered skin tone identifier. The text information entered can include letters, number, or any combination of use. For example, the text can be ASCII characters or a string data type. The virtual keyboard can be automatically hidden by the tablet (e.g., by the application program or tablet operating system) unless text entry is needed.

Figure 18:
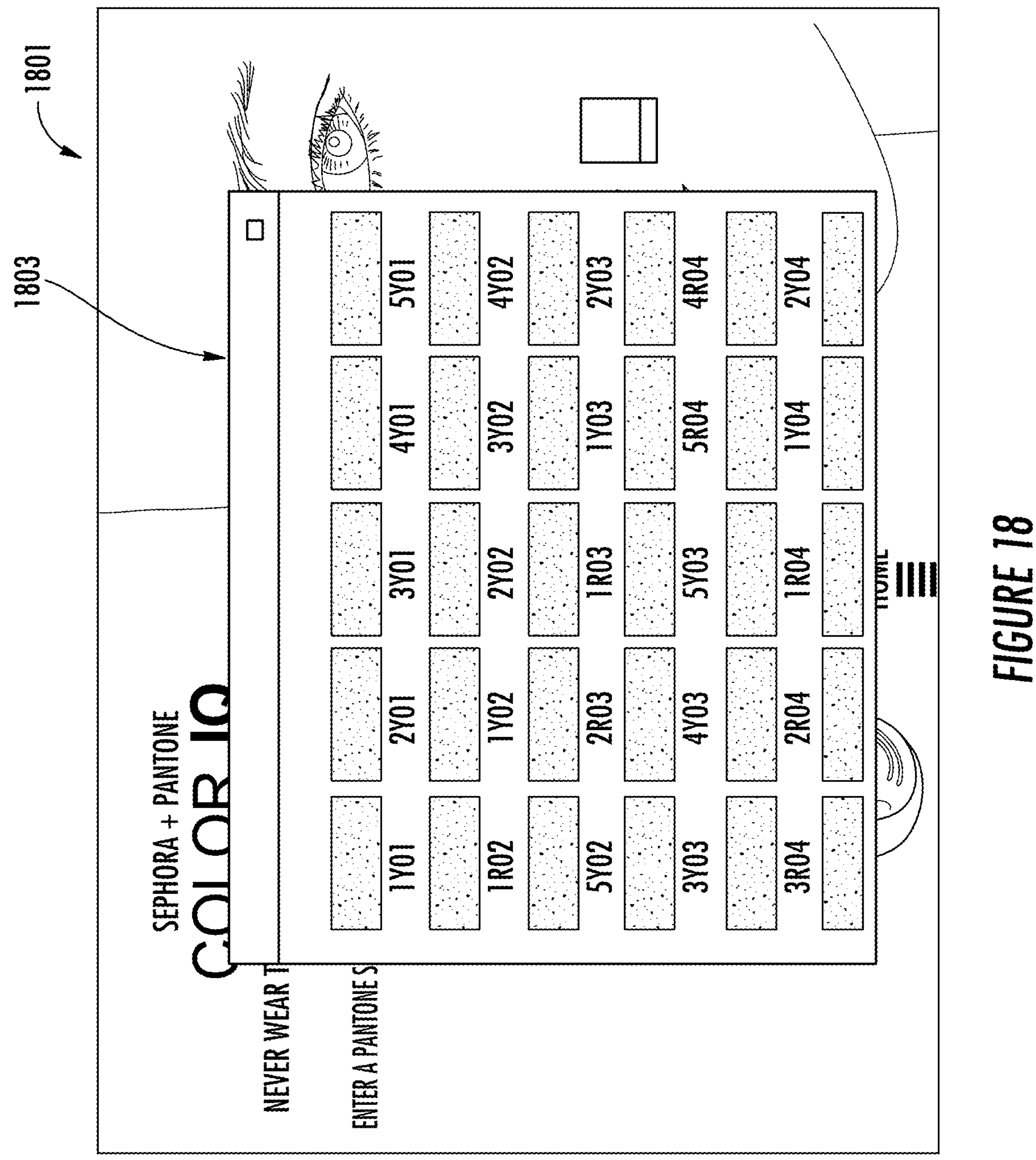
FIG. 18 shows a screen to select a skin tone color shade of the system.

FIG. 18 shows a screen 1801 to select a skin tone color shade of the system. Screen 1801 can be presented when the user selects link 1605 of screen 1601. The system displays at least a portion of a skin tone color set of the system and allows a user to select one of the skin tone identifiers. In screen 1801, an array of thirty skin tone color identifiers (which can be referred to as a skin tone identifier chart) are displayed with their associated skin tone color shades. This is a portion of the available 110 skin tone identifiers. The user selects a skin tone color by selected pointing to the appropriate skin tone color in the array.

In this example, the system displays these color skin tones as a grid (or table) in order of the skin tone color set. Additional color skin tones can be shown by swiping (or dragging) the table upwards or downwards. Other implementations can use a looping or carousel option, allowing the user to go through the skin tone options by swiping the screen.

Figure 19:
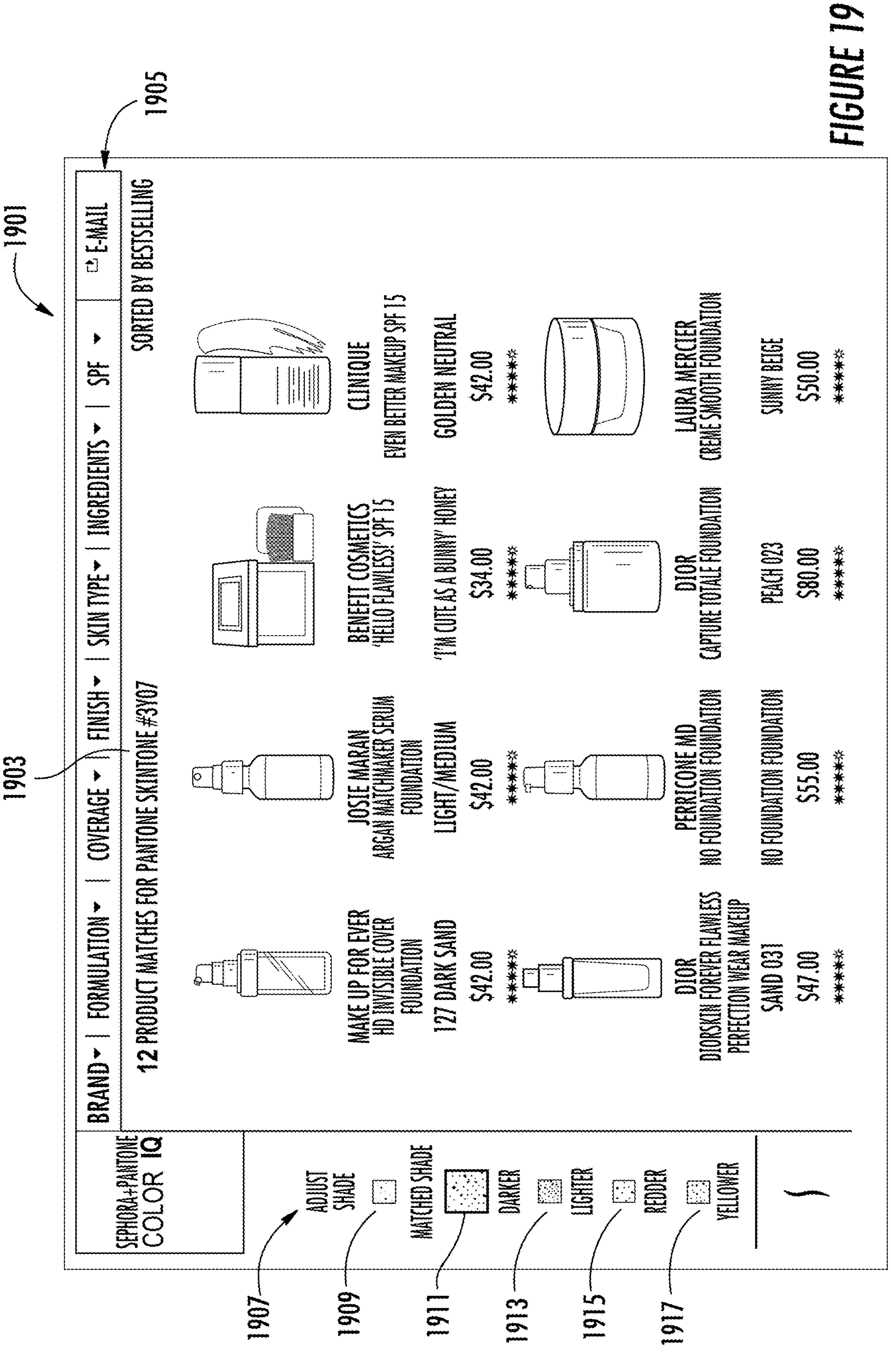
FIG. 19 shows a screen showing various products corresponding to a skin tone identifier.

FIG. 19 shows a screen 1901 showing various products corresponding to a skin tone identifier. This screen is displayed after the user has entered their skin tone identifier, such via screen 1701 or 1801. The products displayed in this figure, provided merely as an example, correspond to skin tone identifier 3Y07 as shown in 1903. The screen shows drop-down menu bar 1905 that includes options for adjusting brand, formulation, coverage, finish, skin type, ingredients, skin protection factor (SPF), and e-mail. The menu bar allows adjusting the various products shown as a filter. Multiple filters can be chosen by the user at once. This allows the user a fine control over details to narrow cosmetic products that work best for them. In other implementations, the drop-down menu bar can be replaced by other interface elements, such as side bars, icons, buttons, check-boxes, and other interface elements.

The system also includes a sidebar 1907 that allows the user to adjust their selected skin tone. The system includes a sample or swatch for the current skin tone selected (3Y07). The system also displays four other swatches 1909, 1911, 1913, and 1915 that represent additional skin tones the user may want to see. These skin tones represent skin tones that are darker, lighter, redder, or yellower than the current skin tone selected. If these options are not available, its respective swatch is not shown.

Figure 20:
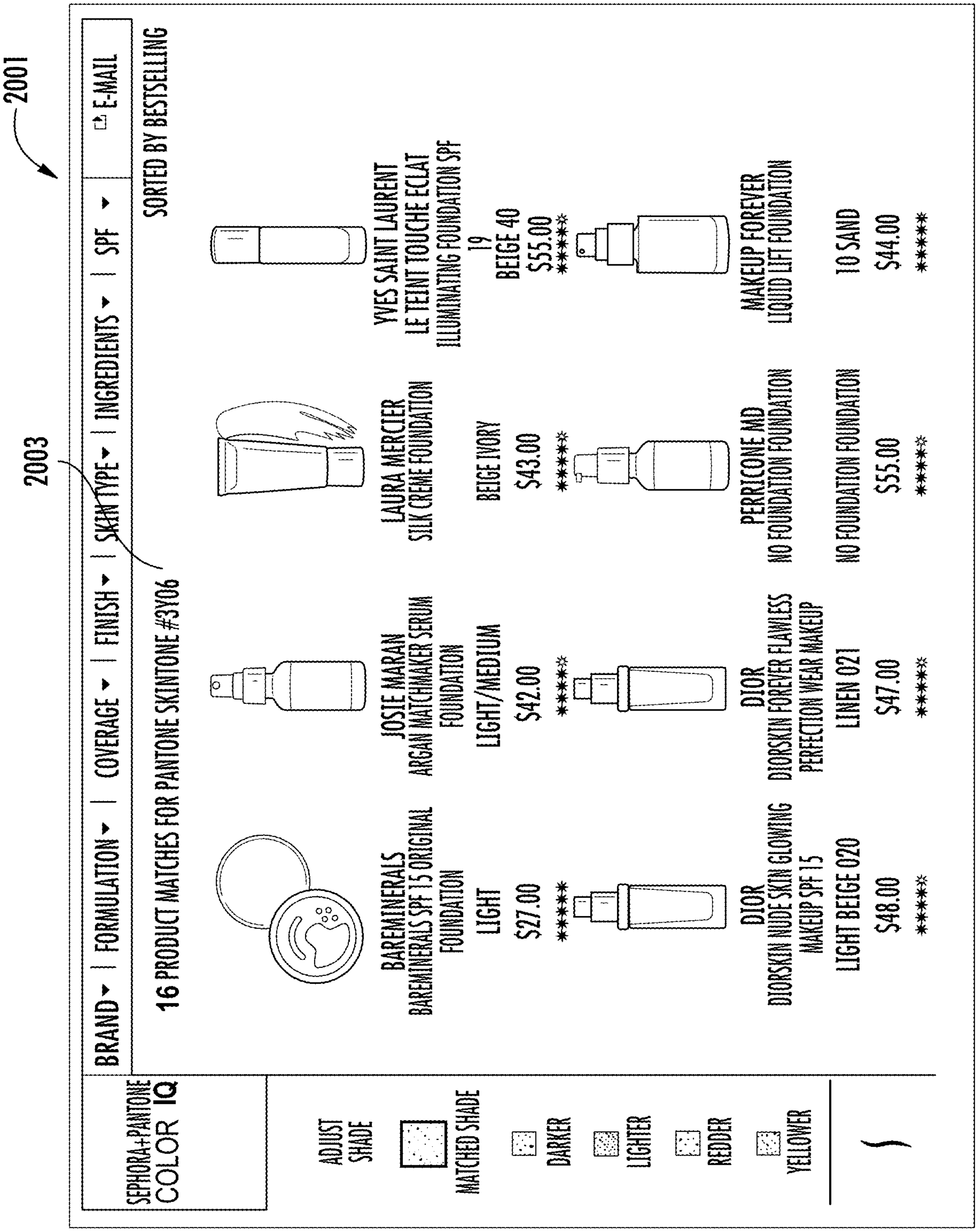
FIG. 20 shows a screen showing various products corresponding to a skin tone identifier.

FIG. 20 shows another screen capture of a screen 2001 showing various products corresponding to a skin tone identifier. For example, if the user viewing screen 1901 decides the skin tone 3Y07 is too dark, the user can select the lighter option from sidebar 1907. The system returns cosmetic product results for 3Y06 (or the skin tone one degree lighter than 3Y07) as shown in 2003.

Figure 21:
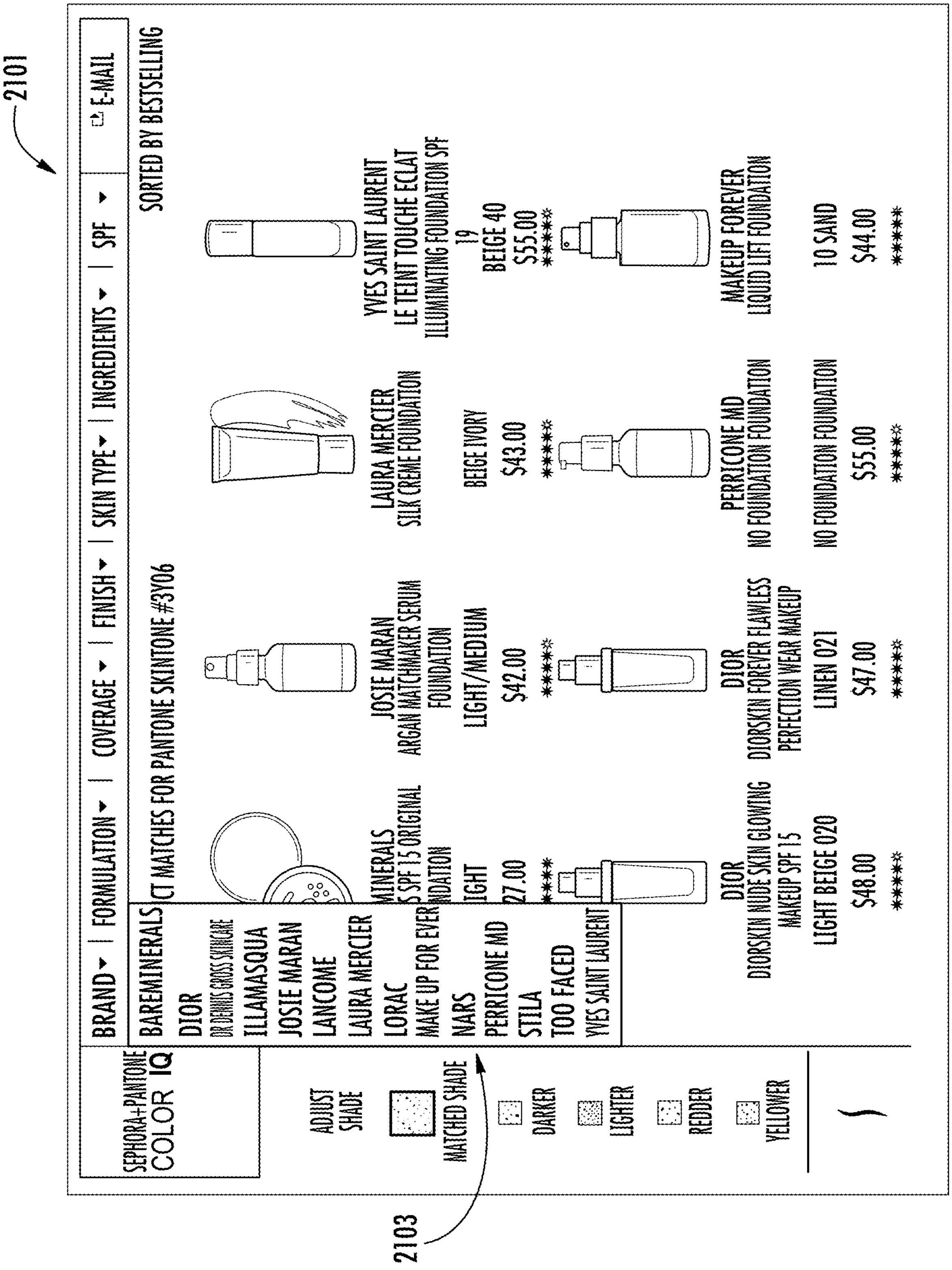
FIG. 21 shows a screen showing options for a filter by brand.
Figure 22:
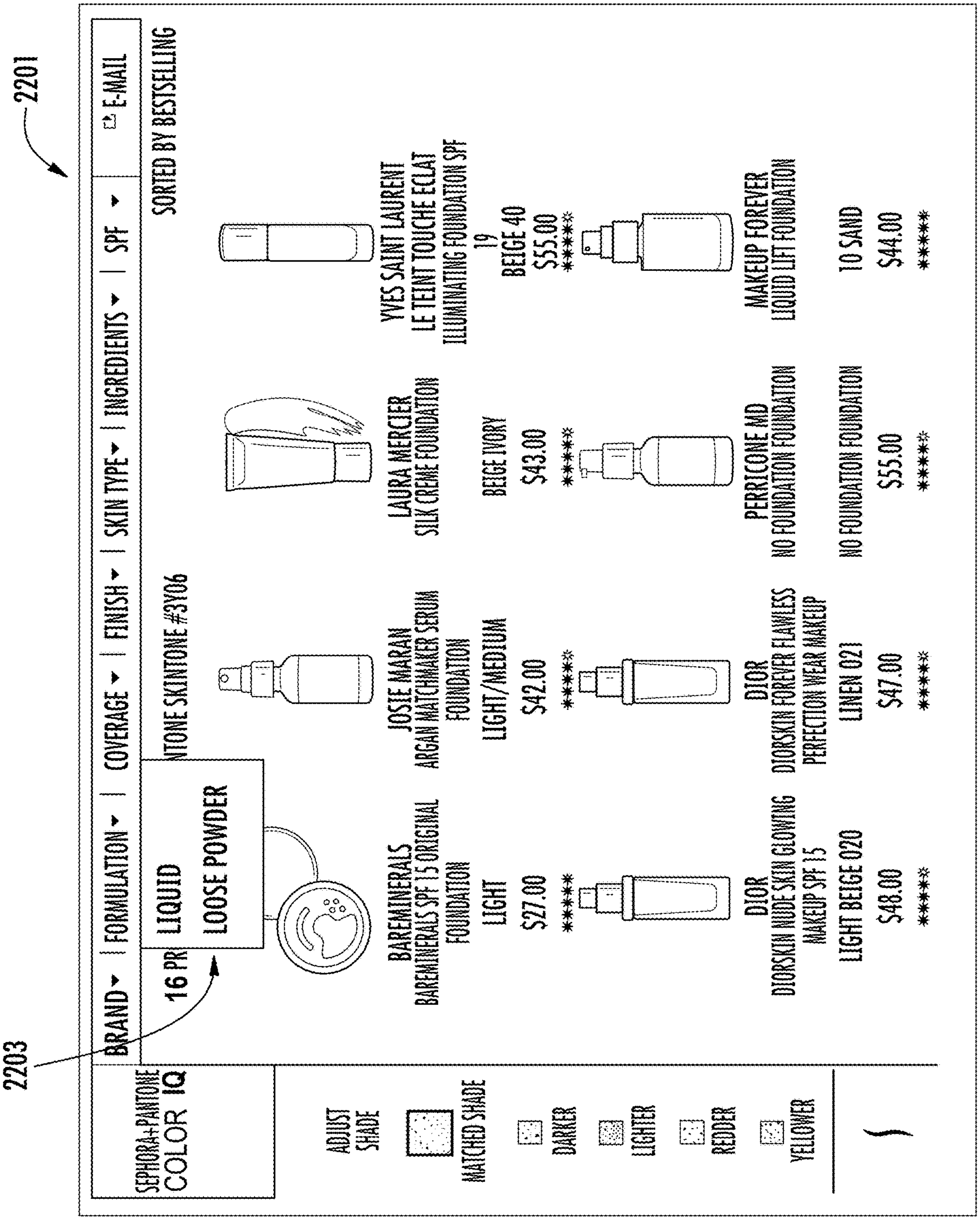
FIG. 22 shows a screen showing options for a filter by formulation.
Figure 23:
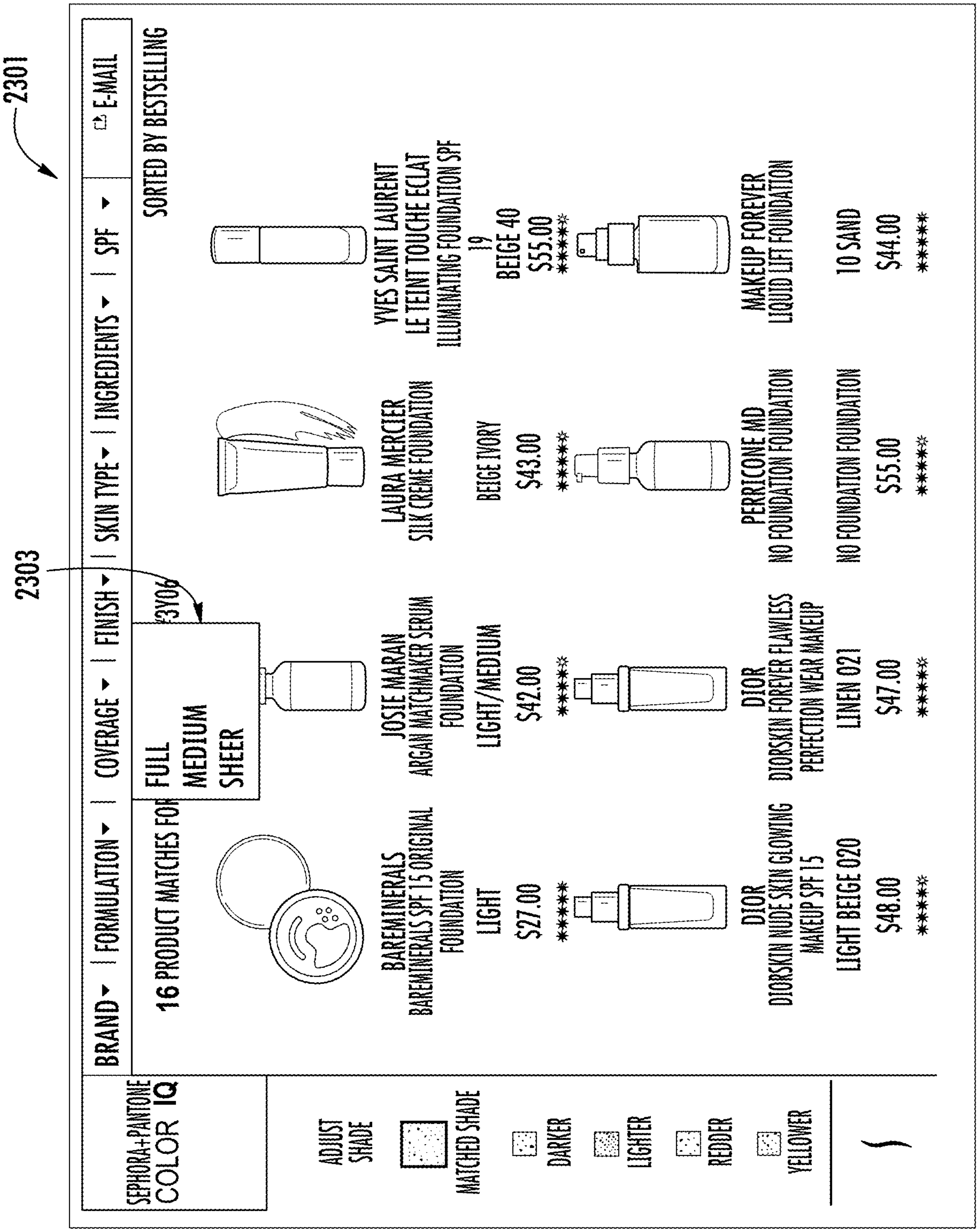
FIG. 23 shows a screen showing options for a filter by coverage.
Figure 24:
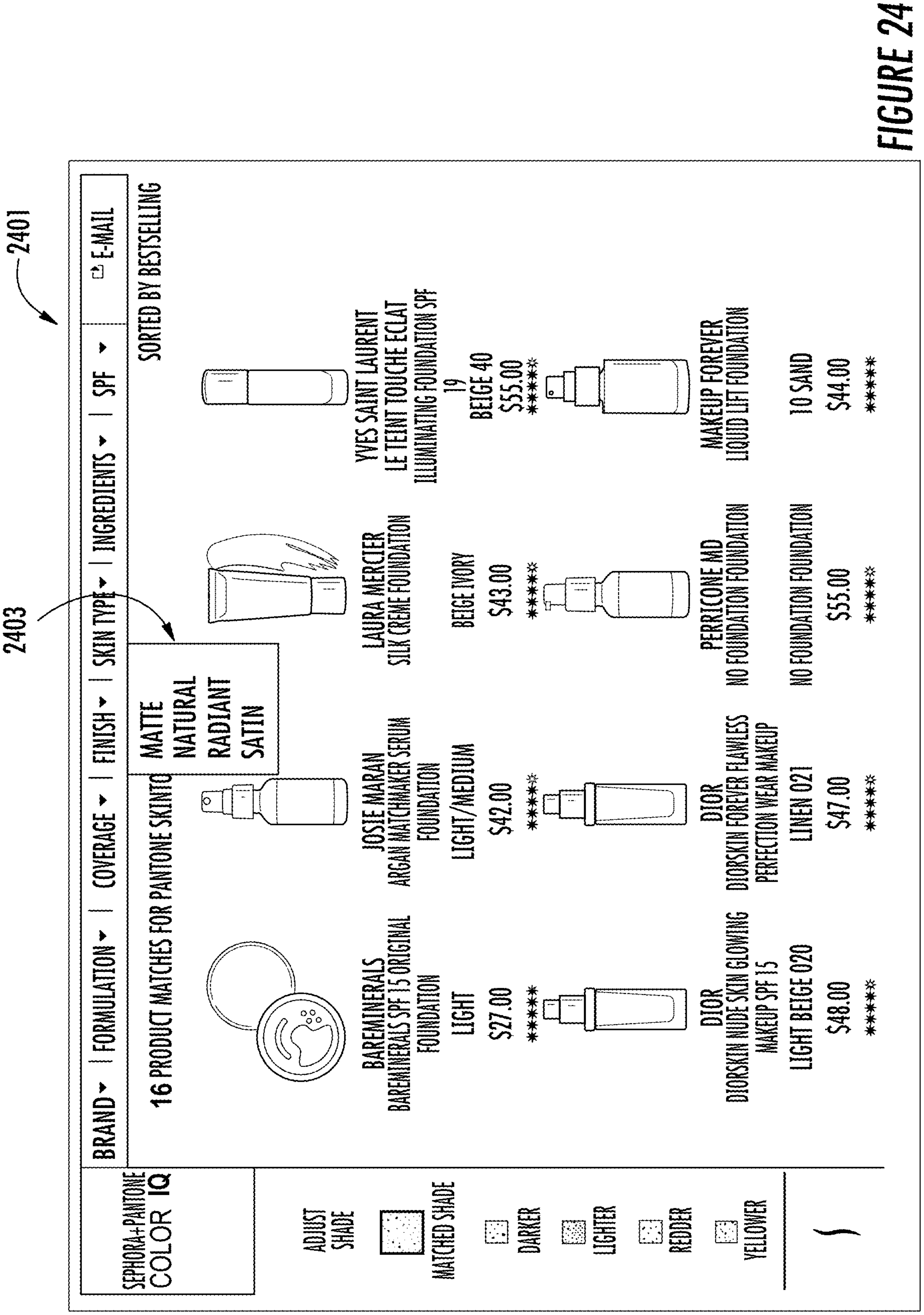
FIG. 24 shows a screen showing options for a filter by finish.
Figure 25:
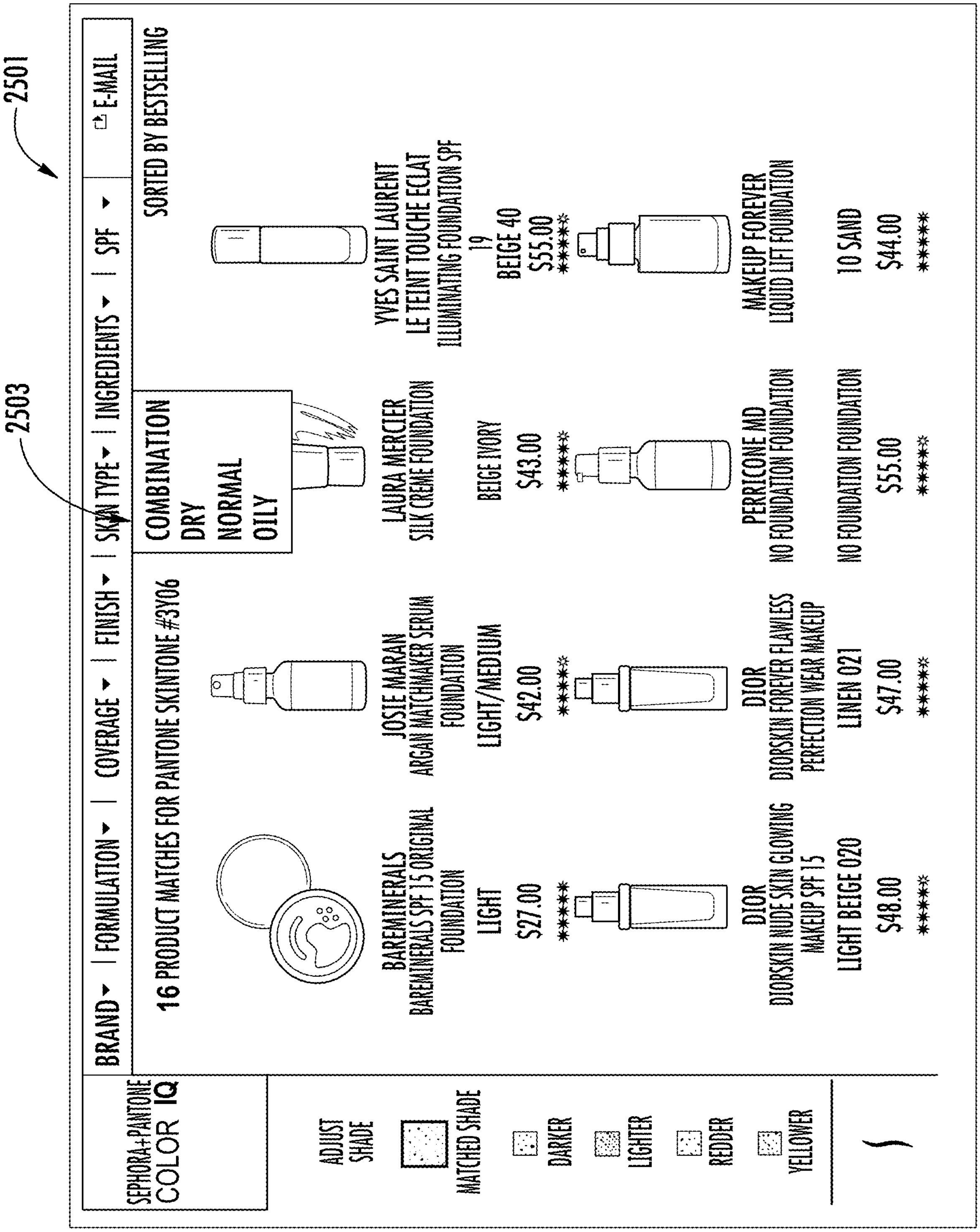
FIG. 25 shows a screen showing options for a filter by skin type.

FIG. 21 shows a screen 2101 showing options for a filter by brand. The options to filter by brand include: BareMinerals, Dior, Nars, and other cosmetic manufacturers. FIG. 22 shows a screen 2201 showing options for a filter by formulation. The options to filter by formulation include: liquid or loose powder. FIG. 23 shows a screen 2301 showing options for a filter by coverage. The options to filter by coverage include: full, medium, or sheer. FIG. 24 shows a screen 2401 showing options for a filter by finish. The options to filter by finish include: matte, natural, radiant, or satin. FIG. 25 shows a screen 2501 showing options for a filter by skin type. The options to filter by skin type include: combination, dry, normal, or oily.

Figure 26:
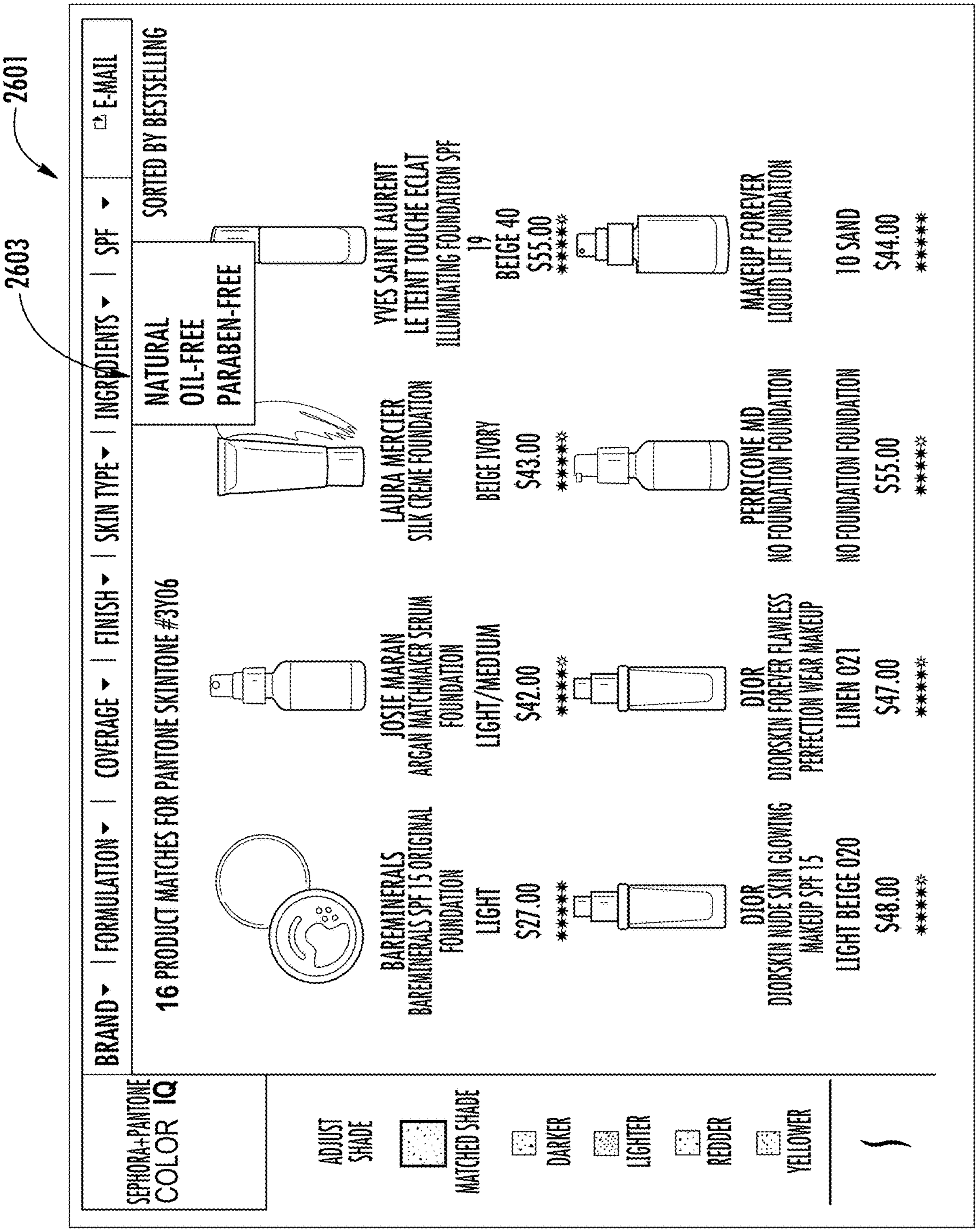
FIG. 26 shows a screen showing options for a filter by ingredients.
Figure 27:
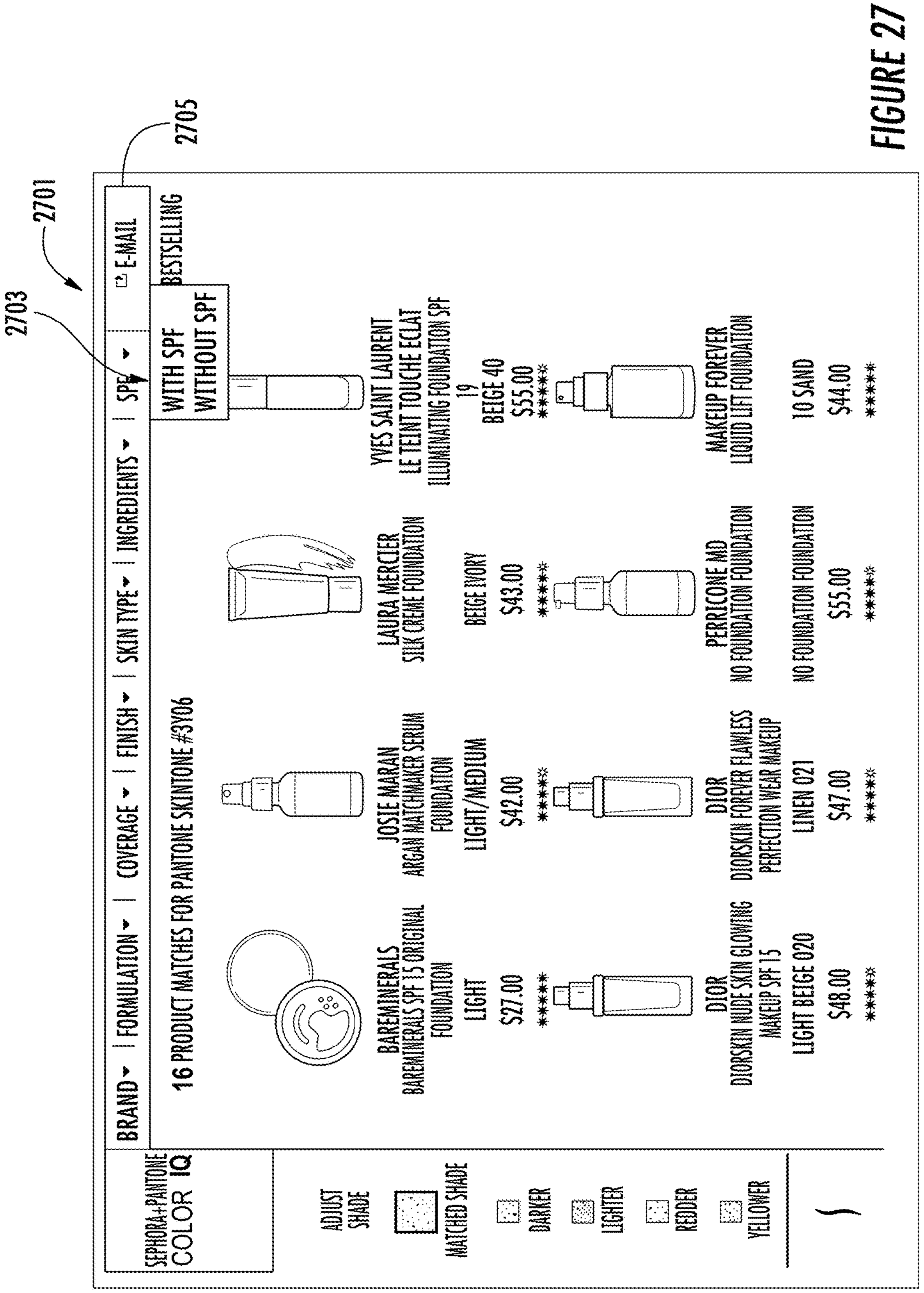
FIG. 27 shows a screen showing options for a filter by sun protection factor.

FIG. 26 shows a screen 2601 showing options for a filter by ingredients. The options to filter by ingredients include: natural, oil-free, or paraben-free. FIG. 27 shows a screen 2701 showing options for a filter by sun protection factor. The options to filter by SPF include: with SPF or without SPF. Button 2705 allows the user to e-mail their results to their personal e-mail or to others. The e-mail includes their skin tone identifier information, as well as any selected products (i.e., products designated as a favorite).

Figure 28:
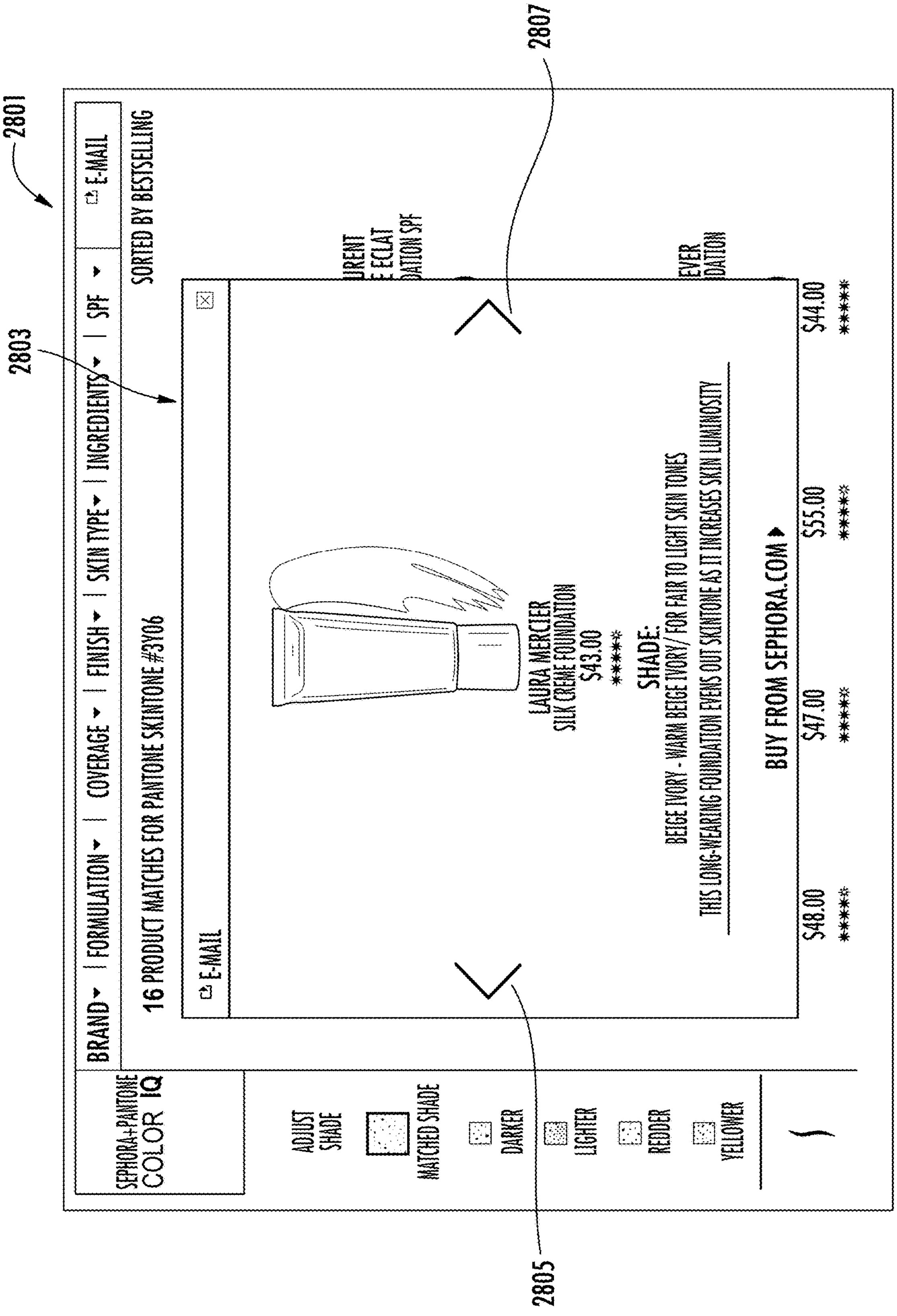
FIG. 28 shows a screen showing a selected cosmetic product.

FIG. 28 shows a screen 2801 showing a selected cosmetic product. The product is shown in a pop-up box 2803 that provides greater detail about the selected cosmetic product. This can include information on specific details of the selected product, its pricing, as well as indicating how others rate the product (i.e., more stars, the more highly rated). Arrows 2805 and 2807 are buttons that allow the user to quickly see other products, without having to return to the grid listing of products.

Figure 29:
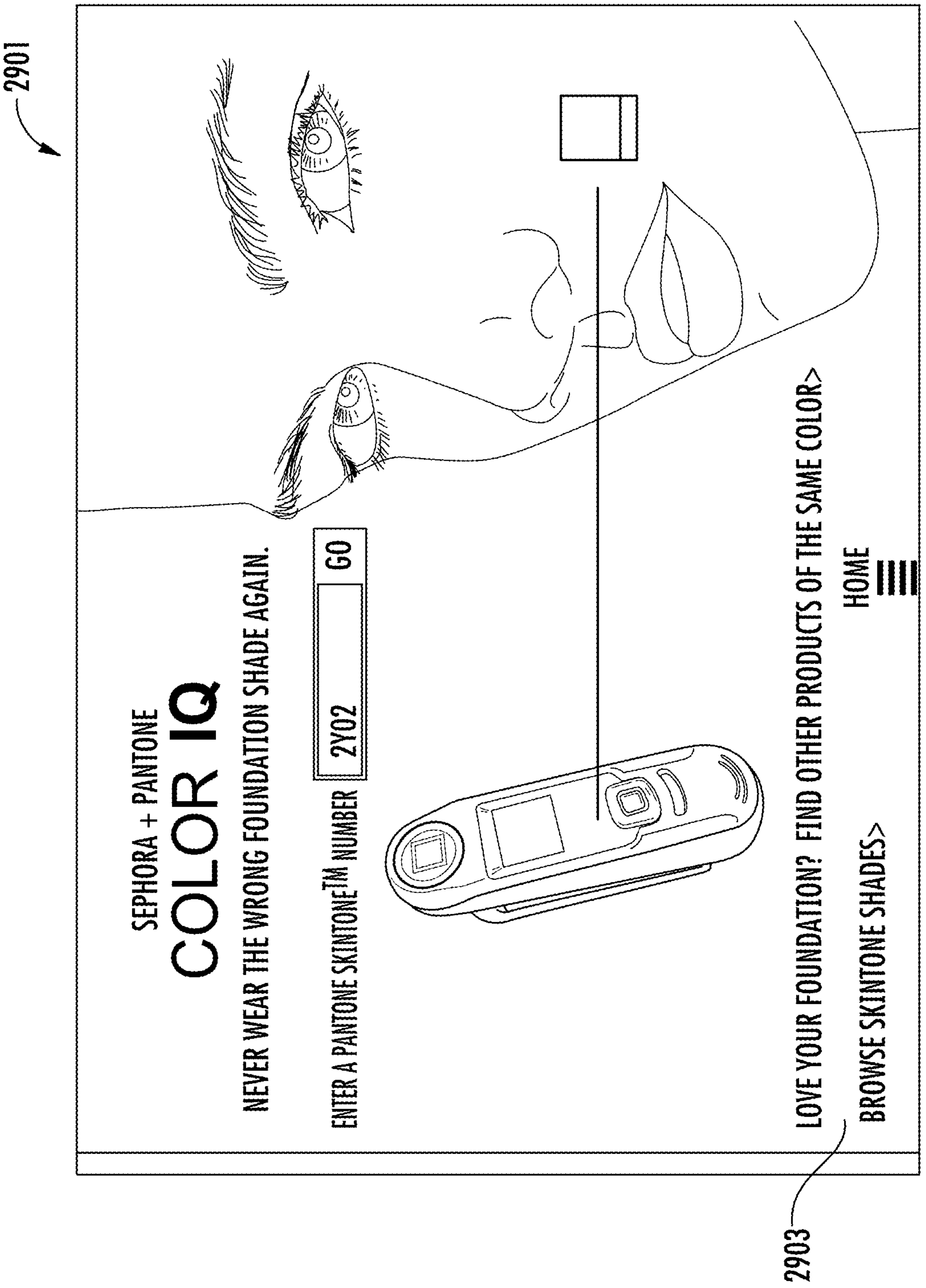
FIG. 29 shows a screen to select a product matching option.

FIG. 29 shows a screen 2901 to select a product matching option. A text link for "Love your foundation? Find other product of the same color >" 2903 allows the user to use a reverse lookup feature of the system. This feature allows users to identify products they may like based on products they already use.

Figure 30:
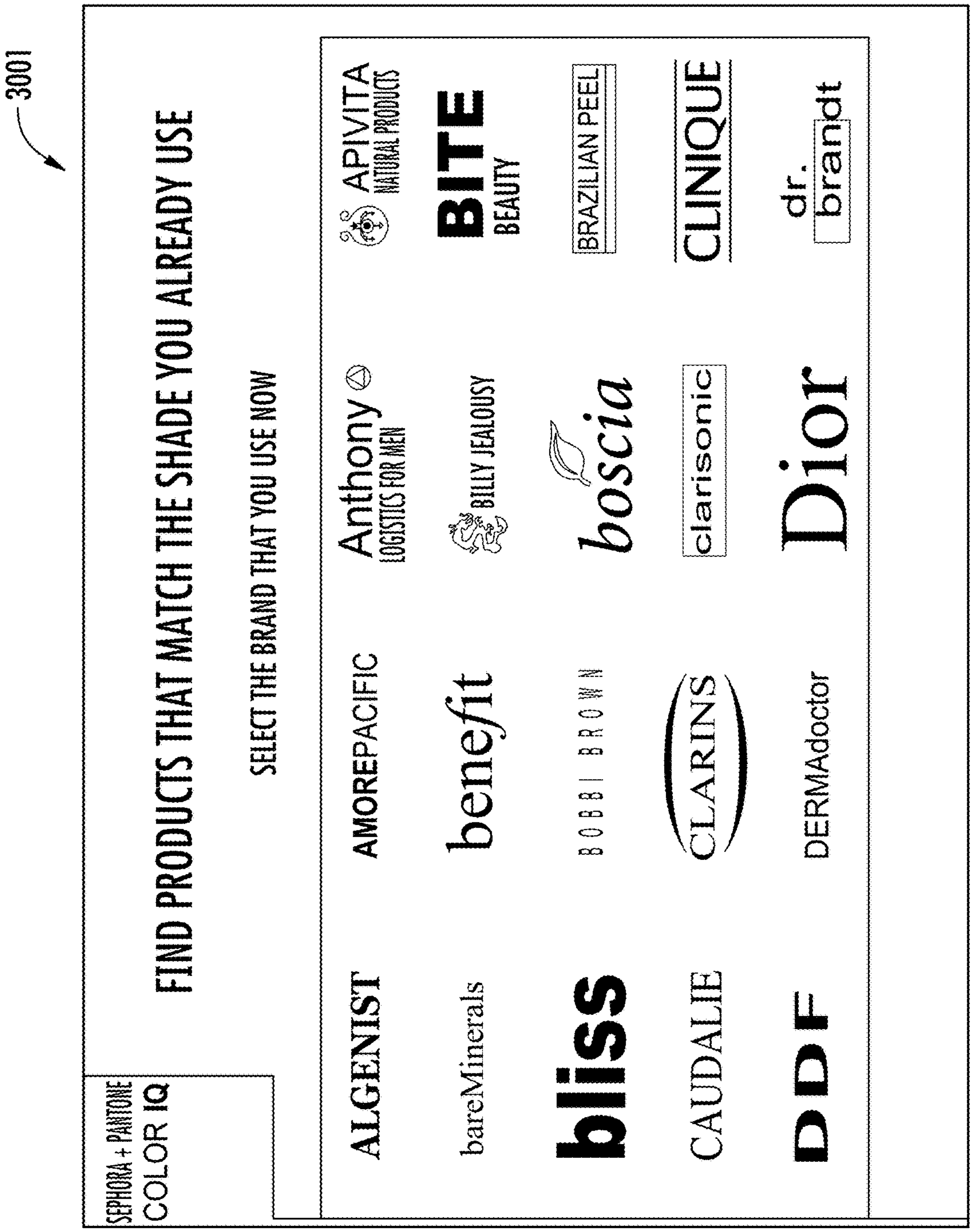
FIG. 30 shows a screen showing various brands of cosmetics.

FIG. 30 shows a screen 3001 showing various brands of cosmetics for a reverse lookup feature. Screen 3001 is displayed after link 2903 is selected. The system prompts the user for a brand of make-up they use. The user can select a button or link representative of the brand of product they use.

Figure 31:
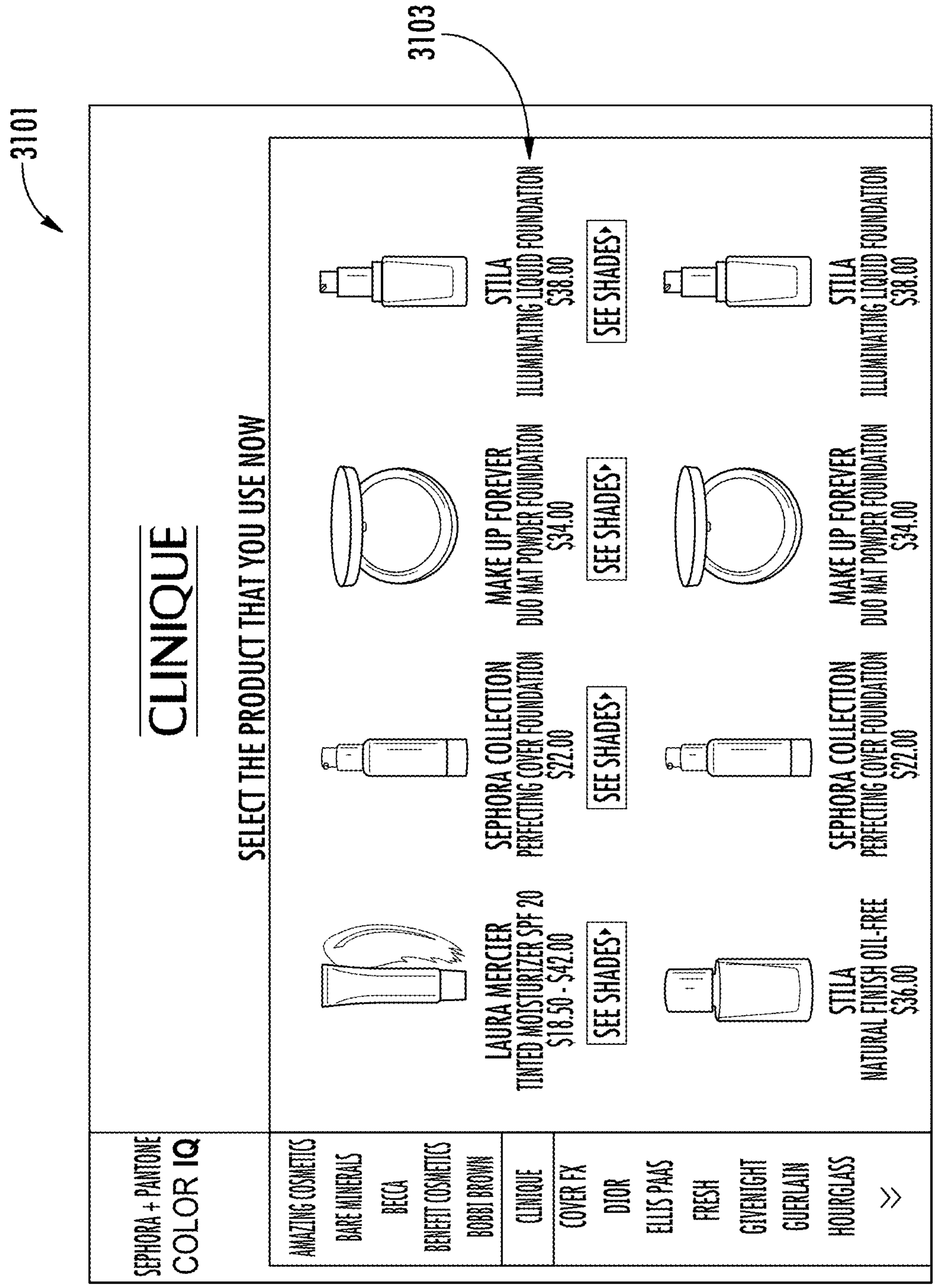
FIG. 31 shows a screen showing various products.

FIG. 31 shows a screen 3101 showing various products. These can be products from the brand selected on screen 3001. After the user selects a link representative of a Clinique brand in screen 3001, the user is presented screen 3101 that shows Clinique products.

Figure 32:
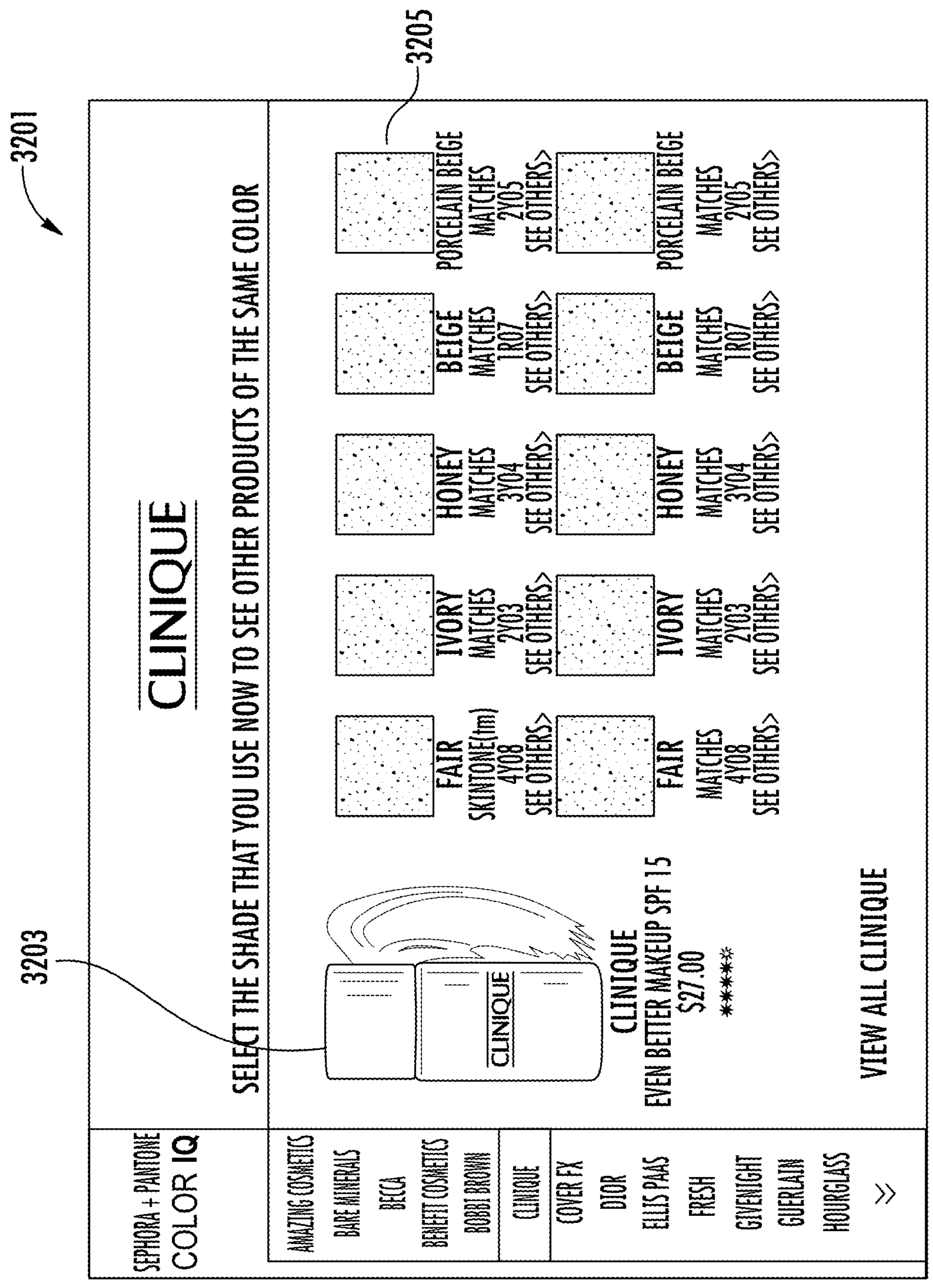
FIG. 32 shows a screen showing options for various shades.

FIG. 32 shows a screen 3201 showing options for various shades. The user is presented this screen after selecting a product button or link from screen 3101. For example, the user selected a product 3203 from screen 3101. The system shows the user shades their selected product is presented in an array grid format 3205. Using this, the user can identify which skin tone identifier their skin corresponds with.

In an implementation, the tablet computing device displays an attractor screen loop when it is not being used. The system can determine the tablet is not in use when a power or other button on the tablet is pressed or when the tablet has not been interacted with for a set period of time (e.g., 10 seconds, 15 seconds, one minute, three minutes, or more). The attractor screen loop can contain pictures or videos that attract clients and explains the system to passersby of the system. This can increase usage of the system and explain the benefits of the system. This also allows the system to clear any personal information that a previous user had left on the tablet device. For example, the previous user's skin tone identifier or other information is cleared when the attractor screen loop begins.

In an implementation, the system allows the user to adjust cosmetic product matches suggested (e.g., a color tone identifier) by the system. This can include allowing a user to adjust their primary and secondary matches suggested by the system. Some example methods to allow the user to adjust their matches are presented flowing:

(1) Ability of the system to display a shade adjustment scale on a screen. The user can adjust on the scale to make their selections lighter or darker, or to make their selections redder or yellower.

(2) Ability of the user to explore the shades with one degree of difference from the system suggestion on the skin tone color set (e.g., skin tone color grid). For example, the user is shown one shade darker (located under the system suggestion), lighter (located above the system suggestion), redder (located left of the system suggestion), or yellower (located right of the system suggestion).

(3) Ability of the system to show only applicable shade adjustor options. For example, if the system suggestion is the darkest selection for a given redness, then no suggestion for a darker skin tone identifier is presented. In another example, if a suggestion is the reddest and darkest in the skin tone color set of the system, the system does not show options for darker or redder color skin identifiers.

(4) Ability of the system to allow a user to select one of the shade adjustor and look-up appropriate product results.

In an implementation, the system includes a photo booth. This allows customers (or other users) to take pictures of themselves (e.g., with their selected cosmetic products applied). The system can be connected with the user's social network accounts (e.g., Facebook, LinkedIn, Google Plus, Pinterest, MySpace, Orkut, Renren, or other networks), allowing posting of the picture onto their social network account. The photo booth can also include functionality to share photos by e-mail. The user's personal e-mail can be used, so that the e-mail is less likely to be identified as spam when being sent to other (e.g., friends, family, coworkers, or others).

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A system comprising:

a skin tone color space, wherein the skin tone color space includes a plurality of skin tone identifiers and each skin tone identifier corresponds to a skin tone found in a population sample;

a scanning device, wherein the scanning device comprises a scanning surface comprising at least a first source and a second source, and a first light sensor and a second light sensor, the first source emits light in a first wavelength spectrum, the second source emits light in a second wavelength spectrum, which is different from the first wavelength spectrum, the first light sensor comprises a sensitivity to a first color spectrum, and the second light sensor comprises a sensitivity to a second color spectrum, which is different from the first color spectrum;

a first measurement, measured using the scanning device from a first location of a customer's skin;

a second measurement, measured using the scanning device from a second location of a customer's skin which is different from the first location; and a skin tone identifier in the skin tone color space, calculated by a blending of the first and second measurements.

2. The system of claim 1 comprising:

a third measurement, measured using the scanning device from a third location of a customer's skin that is different from the first and second locations.

3. The system of claim 2 wherein the skin tone identifier comprises a blending of the first, second, and third measurements.

4. The system of claim 2 wherein the first location comprises a forehead of the customer.

5. The system of claim 2 wherein the second location comprises a cheekbone of the customer.

6. The system of claim 2 wherein the third location comprises an area below a lip of the customer.

7. The system of claim 1 wherein the skin tone color space is stored on a nonvolatile memory of the scanning device.

8. The system of claim 1 wherein the first and second locations are free of facial blemishes.

9. The system of claim 1 wherein the first and second locations are free of irregular pigmentation.

10. The system of claim 1 wherein the first wavelength spectrum comprises visible light, and the second wavelength spectrum comprises infrared light.

11. The system of claim 1 wherein the first light sensor comprises a sensitivity to cyan, and the second light sensor comprises a sensitivity to magenta.

12. The system of claim 1 wherein the first wavelength spectrum comprises ultraviolet light, and the second wavelength spectrum comprises infrared light.

13. A method comprising:

providing a skin tone color space, wherein the skin tone color space includes a plurality of skin tone identifiers;

initializing a scanning device, wherein the scanning device comprises a scanning surface comprising at least a first light source and a second light source, and a first light sensor and a second light sensor, the first light source emits light of a first wavelength, and the second light source emits light of a second wavelength;

the first light sensor comprises a sensitivity to a first wavelength, and the second light sensor comprises a sensitivity to the second wavelength, which is different from the first wavelength;

positioning the scanning device to take a first measurement of a customer using the first and second light sources and first and second light sensors;

positioning the scanning device to take a second measurement of the customer using the first and second light sources and first and second light sensors; and calculating and delivering a skin tone identifier to a display device, wherein the calculating comprises mixing to determine the skin tone identifier in the skin tone color space for the customer based on the first and second measurements.

14. The method of claim 13 wherein the first wavelength comprises visible light, and the second wavelength comprises infrared light.

15. The method of claim 13 wherein the calculating is performed at a server, and the display device is a user's device.

16. A device for determining a skin tone comprising:

a memory portion, storing a skin tone color space, wherein the skin tone color space includes a plurality of skin tone identifiers and each skin tone identifier corresponds to a skin tone found in a population sample;

a scanning portion with a plurality of light emitting elements and a photosensitive sensor, wherein a first light emitting element emits light in a first color spectrum, and a second light emitting element emits light in a second color spectrum, which is different from the first color spectrum; and a processing portion to determine skin tone identifiers, comprising:

receiving at least two skin tone measurements; and averaging the at least two skin tone measurements to determine a skin tone identifier based on the skin tone color space.

17. The device of claim 16 wherein the first color spectrum comprises a first visible light spectrum, and the second color spectrum comprises a second visible light spectrum.

18. The device of claim 16 wherein the first color spectrum comprises a visible light spectrum, and the second color spectrum comprises an ultraviolet light spectrum.

19. The device of claim 16 wherein the at least two skin tone measurements are received at a server.

20. The device of claim 16 wherein the averaging the at least two skin tone measurements to determine a skin tone identifier based on the skin tone color space is performed at a server.

* * * * *